United States Patent
Holmes et al.

(10) Patent No.: US 7,700,524 B2
(45) Date of Patent: Apr. 20, 2010

(54) PERFLUORO SULFONYL HALIDES AND RELATED SPECIES AS POLYMER SUPPORT MODIFIERS

(75) Inventors: Christopher Holmes, Saratoga, CA (US); Yijun Pan, Freemont, CA (US)

(73) Assignee: GE Healthcare Limited, Buckinghamshire (GB)

( * ) Notice: Subject to any disclaimer, the term of this patent is extended or adjusted under 35 U.S.C. 154(b) by 1811 days.

(21) Appl. No.: 10/466,124

(22) PCT Filed: Jan. 11, 2002

(86) PCT No.: PCT/US02/00839

§ 371 (c)(1),
(2), (4) Date: Jul. 10, 2003

(87) PCT Pub. No.: WO02/055026

PCT Pub. Date: Jul. 18, 2002

(65) Prior Publication Data

US 2004/0106151 A1 Jun. 3, 2004

Related U.S. Application Data

(60) Provisional application No. 60/261,525, filed on Jan. 12, 2001.

(51) Int. Cl.
C40B 80/00 (2006.01)
(52) U.S. Cl. ............................ 506/42; 506/32; 502/159; 560/150
(58) Field of Classification Search ................... None
See application file for complete search history.

(56) References Cited

U.S. PATENT DOCUMENTS

| 3,028,534 | A | | 4/1962 | Chilton et al. |
| 4,414,146 | A | | 11/1983 | Olechowski et al. |
| 5,235,028 | A | * | 8/1993 | Barany et al. ............... 528/335 |
| 5,919,523 | A | | 7/1999 | Sundberg et al. |
| 6,127,489 | A | | 10/2000 | Newlander et al. |
| 6,225,480 | B1 | | 5/2001 | Tanaka et al. |
| 6,271,345 | B1 | | 8/2001 | Waldmann et al. |
| 6,710,208 | B2 | | 3/2004 | Salvino et al. |
| 2004/0138495 | A1 | | 7/2004 | Haaf et al. |

FOREIGN PATENT DOCUMENTS

WO WO 98/31716 * 7/1998
WO 98/44329 10/1998

OTHER PUBLICATIONS

Akhtar et al. Solid-phase synthesis on functionalized fluropolymer resins. part I: Naflon resin sulfonamide-immobilized carboxylic acid derivatives and aryl vinyl sulfones. 2000 Tetrahedron Letters 41:4487-4491.*
Harmer et al (1997 Chem. Commun. pp. 1803-1804).*
Akhtar, et.al. Solid-phse synthesis on functionalized fluorophore resins. Part I: Nafion resin sulfonamide-immobilised carboxylic acid derivatives and aryl vinyl sulfones. Tet. Lett., Jun. 2000, vol. 41, pp. 4487-4491.
Smith, E.M. A Polymer-Supported Sily Triflate and Subsequent Functionalization: Sysnthesis and Solid-Phase Diels-Alder Reactions of Silyloxydienes. Tet. Lett., Apr. 1999, vol. 40, pp. 3289-3292.
Hu, et.al. Ester Enolate Claisen Rearrangement Using a Polymer-Supported Silyl Triflate. Tet. Lett., Apr. 1999, vol. 40, pp. 3289-3292.
Zaragoza, Florencio New Sulfur-and Selenium-Based Traceless Linkers—More than just Linkers? Angew. Chem. Int. Ed, Jun. 2000, vol. 39, No. 12, pp. 2077-2079.
Harmer, et.al. Towards the sulfuric acid of solids. Adv. Mater. 1998, vol. 10, pp. 1255-1257.
Yamato, T. Recent developments of perfluorinated resinsulfonic acid (Nafion-H) catalysis in organic synthesis. Recent Res. Devel. In Pur & Allied Chem. 1998, vol. 2, pp. 297-310.
Feiring, et.al. Synthesis of Partially fluorinated monomers and polymers for ion-exchange resins. Journal of Fluorine Chemistry. 1999, vol. 93, pp. 93-101.
IPER for PCT/US02/00839 which was received by applicants Oct. 25, 2004 via facsimile.
Weaver, J.D. et.al. "Supported Fluorocarbonsulfonic Acid Catalysts" Catalysis Today, Amsterdam, NL, vol. 14, Jan. 1, 1992, pp. 195-210.
Jin, S. "Reductive cleavage of resin bound arylsulfonates" Tetrahedron Letters, Elsevier, Amsterdam, vol. 39, No. 22, May 28, 1998, pp. 3651-3654.
Ritter "Synthetic transformations of vinyl and aryl triflates" Synthesis, vol. 8, 1993, pp. 735-762.

* cited by examiner

*Primary Examiner*—Christopher Low
*Assistant Examiner*—Christopher M Gross

(57) ABSTRACT

Activated Supports, support-bound activators, strongly acidic supports, and silylating supports are provided; the activated support having the formula (I) wherein L is a linking group component; X is F, CL, OH, and trisubstituted silyloxy; and the shaded circle represents a solid or semi-solid support. Methods of using the activated supports in solid phase organic sync) thesis are also provided.

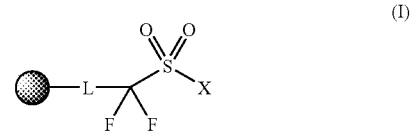

(I)

4 Claims, 7 Drawing Sheets

PERFLUORO SULFONYL HALIDES AND RELATED SPECIES AS POLYMER SUPPORT MODIFIERS

CROSS-REFERENCES TO RELATED APPLICATIONS

This application is a filing under 35 U.S.C. §371 and claims priority to international application number PCT/US02/00839 filed Jan. 11, 2002 which claims priority to U.S. Provisional Application 60/261,525 filed Jan. 12, 2001, the entire disclosure of which is hereby incorporated by reference.

STATEMENT AS TO RIGHTS TO INVENTIONS MADE UNDER FEDERALLY SPONSORED RESEARCH AND DEVELOPMENT

Not applicable

BACKGROUND OF THE INVENTION

The present invention relates to the field of linking groups or activators that are useful in the solid-phase preparation of single compounds and libraries, as well as methods that employ such linking groups and activators. The present invention also relates generally to the use of activated supports and their use in organic solution phase chemistry and as derivatizing agents to aid in chromatography.

Solid phase synthesis has attracted considerable attention from the scientific community, and in particular, the pharmaceutical and agricultural research communities in an effort to speed up the discovery of new biologically active compounds. Critical to the solid phase synthesis of such compounds are the means to attach (and subsequently remove) the compounds from a support. The most frequently used linkers are acid-labile and photo-labile linkers which typically result in the cleaved product having a residual functional group (e.g., carboxylic acid, amide, amine or hydroxy group). Recently, the term "traceless linker" has been used to describe a strategy of releasing compounds from a solid support with little or no trace of the original point of attachment. See James, *Tetrahedron Lett.,* 1999, 55, 4855; Andres, et al., *Curr. Opin. Chem. Biol.,* 1998, 2, 353; Reitz, *Curr. Opin. Drug Discovery Dev.,* 1999; 2, 358; and Zaragoza, *Angew. Chem., Int. Ed.* 2000, 39, 2077.

What is needed in the art are polymer support-linker species that activate certain molecules toward other transformations that would be useful in the preparation of single compounds or compound libraries, and that can also act as traceless linkers.

NAFION™ (Dupont, Wilmington, Del.) is a perfluororesinsulfonic acid that could, in principle be used as a traceless linker in solid-phase organic synthesis. However, the inability to utilize NAFION™ resin in high yields and conversions in solid phase organic synthesis applications has been noted. See Akhtar, et al., *Tetrahedron Lett.* 2000, 41, 4487; Liu, et al., *Tetrahedron Lett.* 2000, 41, 4493. Such limitations include the inability to be wetted or swollen by most aprotic organic solvents. Thus, although NAFION™ is robust and chemically resilient, it is not useful in solid-phase organic synthesis because the perfluoropolymer side chains are not solvated. As a result, there is a need in the art for a polymer-supported perfluorosulfonate that is swellable and wettable by most common solvents.

In addition to being used for solid phase organic synthesis, solid and semi-solid supports are also used in solution phase organic chemistry as catalysts or reagents. For example, in the field of catalysis and organic chemistry, there is widespread use of highly acidic catalysts to promote chemical transformations. These often take the form of polymer supported acids, which can be readily filtered away from a reaction mixture at the completion of the reaction. Resins known to those skilled in the art include polystyrene-based resins, controlled pore glass beads, NAFION™, polyethylene glycol resins, TENTAGEL™ (Rapp Polymere GmbH, Tubingen, Germany), and the like. See Olah, *Synthesis* 1986, 7, 513. Whereas ion-exchange resins, and in particular cation exchange resins, are polymer-supported acids, they are typically based on phenylsulfonic acids and are hence limited in acidity. Perfluorosulfonic acids are dramatically more acidic than phenylsulfonic acids and as such, are quite distinct and often capable of catalyzing a broader range of chemical transformations. Thus, there is a general need in the art for polymer-supported perfluorosulfonic acids and related derivatives.

Processes for making perfluorosulfonic solid acids via encapsulation of perfluorosulfonic acids into hydrocarbon resins have been disclosed in WO 98/30521, however, these are not expected to find application in the field of solid phase organic synthesis because the perfluorosulfonate groups are not covalently bound to the resin.

NAFION™ has been demonstrated to act as a highly acidic supported catalyst. Its properties have been noted by Olah, *Synthesis* 1986, 7, 513; Yamoto, *Recent Res. Devel. In Pure & Applied Chem.* 1998, 2, 297; Harmer, *Adv. Mater.* 1998, 10, 1255. However, NAFION™ and related polymers in the art are not effectively swollen by most aprotic organic solvents. Because NAFION™ is not swellable or wettable by most common organic solvents, only the acid groups on the surface of NAFION™ are available for reaction, while the majority of the acid groups contained within the polymer are unavailable for reaction. One technique of increasing the effective surface area is to grind the polymer into fine particles and to imbed these into an inert carrier such as clay or amorphous silica. See Harmer, *Adv. Mater.* 1998, 10, 1255. These hybrid materials are subject to leaching artifacts and can often be difficult to filter away due to the heterogeneity of the particles. Thus, there is a need in the art for supported superacids that are swollen by common organic solvents, allowing supported superacids to be used for more applications and under milder reaction conditions. See Ishihara, et al., Angew. Chem. Int. Ed. 2001, 40.

A superacid polymer-supported resin that is swellable would be highly desirable due to the ease of use, the enhanced effective acid content (because most or all of the contained acid groups would be available for use), and compatibility with a wide range of solvents.

SUMMARY OF THE INVENTION

The present invention provides a variety of support-bound moieties and activated supports, that have utility in solid phase or solution phase synthesis, biosynthesis, catalysis, purification, analysis, and identification and screening. Each moiety and activated support includes an activator portion that serves as a reactive center and a linking group component that serves to provide a robust linkage between the support and the activator portion. The linking group components further include an activator enhancing portion that serves to increase the reactivity of the activator portion and suitable spacer that provides sufficient distance between the activator portion and the support.

In one aspect, the present invention provides a support-bound activator having the formula:

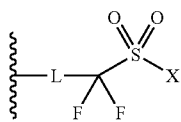

wherein L is a linking group component; X is a member selected from the group consisting of F, Cl, OH, and trisubstituted silyloxy; wherein the support-bound activator is covalently attached to a solid or semi-solid support.

In another aspect, the present invention provides an activated support comprising a solid or semi-solid support; and at least one support-bound activator having the formula:

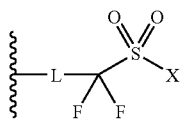

wherein L is a linking group component; X is a member selected from the group consisting of F, Cl, OH, and trisubstituted silyloxy; and wherein the support-bound activator is covalently attached to the solid or semi-solid support.

In another aspect, the present invention provides a support-activated target comprising a solid or semi-solid support; an activating group covalently attached to the solid or semi-solid support, wherein the activating group has the formula:

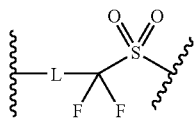

wherein L is an linking group component; and a target group covalently attached to the activating group; wherein the target group can be cleaved from the activating group by a nucleophile.

In another aspect, the present invention provides a library of support-activated targets comprising a plurality of support-activated target members, wherein each support-activated target member further comprises a solid or semi-solid support; an activating group covalently attached to the solid or semi-solid support, wherein the activating group has the formula:

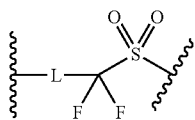

wherein L is an linking group component; and a target group covalently attached to the activating group; wherein the target group of at least one support-activated target member in the library is different from the target group of at least one other support-activated target member in the library.

In another aspect, the present invention provides a strongly acidic support comprising a solid or semi-solid support; and at least one support-bound strongly acid group having the formula:

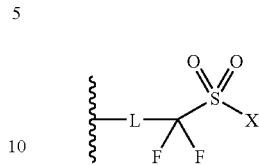

wherein L is a linking group component; and X is OH; and wherein the support-bound strongly acid group is covalently attached to the solid or semi-solid support.

In another aspect, the present invention provides a silylating support comprising a solid or semi-solid support; and at least one support-bound silylating group having the formula:

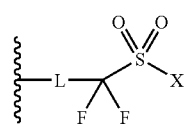

wherein L is a linking group component; X is a trisubstituted silyloxy; wherein the support-bound silylating group is covalently attached to the solid or semi-solid support.

In yet another aspect, the present invention provides a method for covalently attaching a nucleophile to a compound having a hydroxy group or an enolizable ketone, the method comprising, (a) contacting a compound having a hydroxy group or an enolizable ketone with a support-bound activator, wherein said contacting a compound having a hydroxy group or an enolizable ketone with a support bound activator forms an activated complex; and (b) contacting the activated complex with a reagent comprising a nucleophile under conditions sufficient to covalently attach the nucleophile to the compound.

In still another aspect, the present invention provides a linker reagent having the formula:

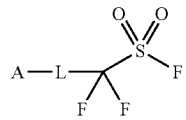

wherein L is a linking group component; and A is an attaching group.

DETAILED DESCRIPTION OF THE INVENTION

Figure 1:
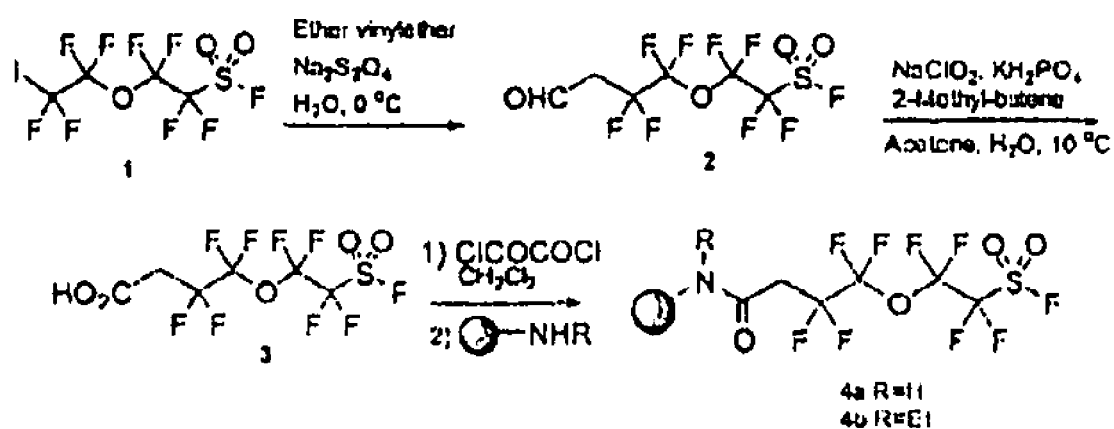
FIG. 1 illustrates a synthetic scheme for the preparation of a support-bound perfluorosulfonyl fluoride linker in accordance with the present invention.

In accordance with the present invention and as used herein, the following terms and abbreviations are defined with the following meanings, unless explicitly stated otherwise. These explanations are intended to be exemplary only. They are not intended to limit the terms as they are described or referred to throughout the specification. Rather these explanations are meant to include any additional aspects and/or examples of the terms as described and claimed herein.

The following abbreviations are used herein: AcOH or HOAc, acetic acid; Boc, t-butoxycarbonyl; DMF, dimethylformamide; EtOAc, ethyl acetate; NMP, N-methylpyrrolidone; TFA, trifluoroacetic acid.

The term "support-bound activator" as used herein refers to an activator which is attached to a solid or semi-solid support by at least one covalent bond. The term "activator" as used herein refers to a chemical moiety which activates, or increases the chemical reactivity of, another portion of a molecule. The term "support-bound activator" is not meant to limit the location of the support-bound activator on the solid or semi-solid support; that is, the support-bound activator can be covalently attached to the surface portion of the solid or semi-solid support or the support-bound activator can be covalently attached to any internal portion of the solid or semi-solid support. In other words, the support-bound activator can be covalently attached to any portion of the solid or semi-solid support.

The term "activator portion" as used herein refers to the portion of an activator that increases the chemical reactivity of the activator. In a preferred embodiment, an activator portion comprises the moiety ($-CF_2-SO_2-X$). Activator portions may have analogous counterparts known in the art of solution phase chemistry.

The term "linking group component" as used herein means a moiety that links together a plurality of other moieties. Thus, in one embodiment of the present invention, one portion of a linking group component in a surface-bound activator will have at least one covalent bond with the solid or semi-solid support, and another portion of the linking group component will have at least one covalent bond with an activator portion. Furthermore, the linking group component of a surface-bound activator may have a covalent bond with a plurality of activator portions. Preferably, the linking group component provides suitable spacing for the activator portion to interact with molecules exposed to the activator. The linking group component is preferably 6-50 atoms long, more preferably 8-40 atoms long, even more preferably 8-30 atoms long, and yet more preferably 8-20 atoms long. Additionally, the linker reagent, prior to reaction with the solid or semi-solid support, will include a linking group component; this linking group component will have one portion that has at least one covalent bond with an attaching group and another portion with at least one covalent bond with an activator portion. The term "attaching group" as used herein refers to that portion of a linker reagent that can form a covalent bond with the solid or semi-solid support.

The term "activator enhancing portion" as used herein refers to that portion of the linking group component that increases the chemical reactivity of the activator portion of a support-bound activator. An activator enhancing portion may also extend the length of the linker group component, and additionally, effect the motility of the surface-bound activator.

The terms "solid" or "semi-solid support" as used herein refers to any form of a polymer or composite material that does not completely dissolve in a solvent. By way of example only, a solid or semi-solid support includes colloids (isolated or in suspension), gels, resins, films, as well as any other form of a polymer or composite materials that retains a distinct identity apart from the solvent. The term is not meant to limit in any manner the size, shape, form, or chemical structure of the polymeric or composite material. Such polymeric or composite materials are well known in the art, including, by way of example only, cellulose, pore-glass, silica, polystyrene, polystyrene cross-linked with divinylbenzene, polyacrylamide, latex, dimethylacrylamide, dimethylacrylamide cross-linked with N,N'-bis-acryloyl ethylene diamine, glass, glass coated with a hydrophobic polymer, composites, or any other material conventionally used in solid phase organic synthesis. A valuable reference in this regard is the Novabiochem 2000 catalog, which is incorporated herein by reference. In addition, the term solid or semi-solid support is not limited by the presence and nature of cross-linking groups, and by the nature of the exposed functional groups. Exposed functional groups are moieties on the solid or semi-solid support that can react with linker reagents to form support-bound activators; preferred exposed functional groups include —OH, —SH, —NH$_2$, silyloxy, NHR, NH$_2$NH, CO$_2$H, CO$_2$R, C(O)H, —Br, —I, halomethyl, and alkenyl. Furthermore, the exposed functional groups can be located on the surface of the solid or semi-solid support or dispersed throughout the solid or semi-solid support. In one embodiment, the solid or semi-solid support has a rigid or semi-rigid surface.

The term "particulate support" as used herein refers to a type of solid or semi-solid support that is in the form of small particles. The term is not meant to limit the shape of the solid or semi-solid support. Thus, by way of example only, a particulate support can be a sphere, disk, pellet, sheet, plug, pin, crown, lantern, capillary, hollow fiber, needle, solid fiber, in a beaded or non-beaded form, a resin, a gel, a microsphere, an amorphous shape, or any other conventional form. As one skilled in the art will readily recognize, the scope of the present invention is not limited to the form or shape of the particulate support. The term "particulate support" is not meant to limit the chemical structure of the solid or semi-solid support, and can be composed of any polymer, composite, cross-linker, if any, and exposed functional group. Thus, by way of example only, a particulate support can be composed of cellulose, pore-glass, silica, polystyrene, polystyrene cross-linked with divinylbenzene, polyacrylamide, latex, dimethylacrylamide, dimethylacrylamide cross-linked with N,N'-bis-acryloyl ethylene diamine, glass, glass coated with a hydrophobic polymer, composites, or any other material conventionally used in solid phase organic synthesis. A valuable reference in this regard is the Novabiochem 2000 catalog, which is incorporated herein by reference. A particulate support may also be porous, deformable, hard, wettable, or swellable. The particles will generally be at least 20 micron, preferably at least 75 micron, and more preferably at least 100 micron in diameter. A particulate support will generally maintain its mechanical integrity during use, have functional groups that can react with active species, allow for the serial synthesis of attached targets, can be readily mixed and separated, and will allow for convenient detachment of tags and products. The solid or semi-solid supports may be used as single particle, as groups of particles, as free flowing particles, and may be packed into columns, tubes or other flow-through devices.

The term "resin" as used herein refers to any of a class of solid or semi-solid organic products of natural or synthetic origin, generally of high molecular weight with no definite melting point. A resin may be chemically inert toward reagents and solvents used in solid phase syntheses or may be functionalized with reactive moieties. Resins may swell extensively in solvents.

The term "gel" as used herein refers to a colloidal suspension of a liquid in a solid, forming a jellylike material having properties of both solid and a solution.

The term "colloid" as used herein a substance consisting of very tiny particles suspended in a continuous medium, such as a liquid, a solid, or a gaseous substance. Generally, the diameter of a colloidal particle is from 20 nm to 200 micron, more preferably 100 nm to 200 micron, even more preferably 500 nm to 200 micron, and yet even more preferably 1 micron to 200 micron.

The term "microsphere" as used herein refers to any material which is roughly spherical in shape. Microspheres may be processed, machined, milled, ground, or extruded according to processes known in the art.

The term "superacid" as used herein is a solution of a strong acid in a very acidic solvent. A superacid is an acid that exhibits strength greater than that of 100% $H_2SO_4$.

The term "controlled pore glass" as used herein refers to a glass used as an inorganic support. Controlled pore glass is produced from a borosilicate base material which is heated to separate the borates and the silicates. The borates are leached out from the material, leaving the silica glass with uniform, controlled pores. Controlled pore glasses have excellent mechanical properties, and can be prepared with a wide range of porosities and average pore sizes. They can be modified to include a variety of functional groups.

The term "polyacrylamide" or PAM as used herein refers to a synthetic water-soluble polymer made from monomers of acrylamide. PAM may be fashioned into gels having a variety of pore sizes.

The term "polyethylene glycol" or "PEG" as used herein refers to a water-soluble, waxy polymer comprising subunits HO—$(CH_2CH_2O)_n$H. The term "poly(ethyleneglycol) monomethyl ether" as used herein refers to $CH_3O$ $(CH_2CH_2O)_n$H and may be referred to as methyl-capped PEG. A skilled artisan will recognize that other capped PEGs may be employed without departing from the spirit of the invention.

The term "silica gel" as used herein refers to silicic acid or precipitated silica. Silica gel is an amorphous powder insoluble in water and organic solvents. Silica gel can adsorb up to about 40% of its weight in moisture.

The term "cellulose" as used herein refers to one of many polymers found in nature, as for example in wood, paper, and cotton. Cellulose is a polysaccharide and comprises repeating units of the monomer glucose. Cellulose may be crosslinked and derivatized, e.g., as in methylcellulose.

The term "acrylic acid grafted polypropylene" as used herein refers to a material comprising a polypropylene backbone and polyacrylate, e.g. acrylic acid side chains. One process modifying the properties of polyolefins comprises the "grafting" of polar monomers onto the polyolefin.

The term "target group" as used herein refers to a moiety covalently bound to a support-bound activator. According to one embodiment of the present invention, a support-bound target comprises a target group covalently attached to support as disclosed herein.

The term "cleaved from" as used herein refers to a plurality of transformations disclosed herein in which a target group is removed from an activated support. According to one embodiment of the invention, a support-bound target group is cleaved from or released from a support-bound activator.

The term "polystyrene support" as used herein refers to polymerized monomers of styrene. A polystyrene support may take the form of beads as described herein. A polystyrene support may comprise a cross-linked copolymer of styrene and divinyl benzene.

The term "polystyrene modified by polyethylene glycol" as used herein refers to a polystyrene polymer or cross-linked polystyrene polymer grafted with ethylene glycol monomer or ethyleneglycol polymer (EG). An example of a polystyrene modified by polyethylene glycol is TENTAGEL™ resin.

The term "grafted" as used herein refers to a process wherein monomers or polymers are covalently bonded to an existing polymer.

The term "TENTAGEL™" as used herein refers to a family of grafted copolymers consisting of a low crosslinked polystyrene matrix on which polyethyleneglycol (PEG) is grafted. Because PEG is a polymer with both hydrophobic and hydrophilic properties, the graft copolymer shows modified physico-chemical properties. A TENTAGEL™ resin may comprise about 50-70% PEG (w/w). Therefore, many chemical and physical properties of these polymers are highly dominated by the properties of PEG and not by the hydrophobic polystyrene support. Other related members of this family, for the purpose of this invention, include ARGOGEL™ resin (Argonaut Technologies, Foster City, Calif.), ARGOPORE™ resin (Argonaut Technologies, Foster City, Calif.), HYPOGEL™ resin (Rapp Polymere GmbH, Tubingen, Germany), and JANDAJEL™ resin (Scripps Research Institute, La Jolla, Calif.).

The term "protecting group" as used herein, refers to any of the groups which are designed to block one reactive site in a molecule or moiety while a chemical reaction is carried out at another reactive site. More particularly, the protecting groups used herein can be any of those groups described in Greene, et al., Protective Groups In Organic Chemistry, 2nd Ed., John Wiley & Sons, New York, N.Y., 1991, which is incorporated herein by reference. The proper selection of protecting groups for a particular synthesis will be governed by the overall methods employed in the synthesis and such practice is well known to those skilled in the art. The term "protected forms thereof" as used herein refers to a moiety to which a protecting group has been attached.

The term "unsubstituted" refers to molecules or moieties that do not have additional moieties attached to the named group other than the root compound. Thus, an unsubstituted $(C_1-C_8)$alkyl group consists only of from 1 to 8 alkyl carbon atoms with attached hydrogens.

The term "optionally substituted" or "substituted" refers to molecules or moieties substituted by one to four substituents, independently selected from lower alkyl, lower aryl, lower aralkyl, lower alicyclic, hydroxy, lower alkoxy, lower aryloxy, perhaloalkoxy, aralkoxy, heteroaryl, heteroaryloxy, heteroarylalkyl, heteroaralkoxy, azido, amino, guanidino, halo, lower alkylthio, oxo, acyloxy, aminoalkyl, alkylaminoaryl, alkylaminoalkyl, alkoxyaryl, arylamino, aralkylamino, phosphono, sulfonyl, carboxamidoalkylaryl, carboxamidoaryl, hydroxyalkyl, haloalkyl, alkylaminoalkylcarboxy, aminocarboxamidoalkyl, cyano, lower alkoxyalkyl, lower perhaloalkyl, and arylalkyloxyalkyl.

The term "lower" referred to herein in connection with organic radicals or compounds respectively defines such as with up to and including 10 carbon atoms, preferably up to and including 6 carbon atoms, and advantageously one to four carbon atoms. Such groups may be straight chain, branched, or cyclic.

The term "alkyl" refers to a saturated hydrocarbon radical which may be straight-chain (for example, methyl, ethyl, propyl or butyl) or branched-chain (for example, isopropyl, t-amyl, or 2,5-dimethylhexyl) or cyclic (for example, cyclobutyl, cyclopropyl or cyclopentyl). This definition applies both when the term is used alone and when it is used as part of a compound term, such as "aralkyl" and similar terms. Preferred alkyl groups are those containing from 1 to 8 carbon atoms, and are referred to as a "$(C_1-C_8)$alkyl" group. Other preferred alkyl groups include those containing from 1 to 20 carbon atoms. All numerical ranges in this specification and claims are intended to be inclusive of their upper and lower limits. The alkyl group may be optionally substituted.

The term "alkylene" as used herein refers to a divalent carbon moiety, e.g., $CR_2$. Alkylene groups be linked to form straight chain alkyl groups and may be optionally substituted with up to two substituents per carbon atom.

The term "alkenyl" as used herein refers to a moiety which contains one or more sites of unsaturation. The term "alkenyl" as used herein may also refer to a moiety which contains at least one carbon-carbon double bond and includes straight-chain, branched-chain and cyclic groups. Alkenyl groups may be optionally substituted. The terms "vinyl" and "olefinic" are sometimes used interchangebly with the term alkenyl.

The term "$(C_1-C_8)$alkenyl" as used herein refers to an alkenyl group having from 1 to 8 carbon atoms. Such groups may be straight chain, branched, or cyclic. A $(C_1-C_8)$alkenyl group may be optionally substituted.

The term "alkynyl" as used herein refers to a moiety that contains at least one carbon-carbon triple bond and includes straight-chain, branched-chain and cyclic groups. Alkynyl groups may be optionally substituted.

The term "$(C_1-C_8)$alkynyl" as used herein refers to an alkynyl group having from 1 to 8 carbon atoms. Such groups may be straight chain, branched, or cyclic. A $(C_1-C_8)$alkynyl group may be optionally substituted.

The term "aryl" as used herein refers to a moiety having either a single ring or multiple rings which are fused together and which has at least one ring having a conjugated pi electron system; the multiples rings may also be linked covalently or via a common group such as an ethylene or methylene moiety. Aryl groups may be optionally substituted at any position on the ring which would otherwise be occupied by a hydrogen atom.

The term "trisubstituted silyloxy" as used herein refers to a moiety having the formula $—OSiR^3R^4R^5$, wherein, each of $R^3$, $R^4$, and $R^5$ is independently a member selected from the group consisting of substituted $(C_1-C_8)$alkyl, unsubstituted $(C_1-C_8)$alkyl, substituted $(C_1-C_8)$alkenyl, unsubstituted $(C_1-C_8)$ alkenyl, substituted aryl, and unsubstituted aryl.

The term "heteroalkyl" refers to an alkyl radical or group in which 1, 2, or 3 of the carbon atoms in the main chain of atoms has been replaced by a heteroatom selected from oxygen, nitrogen, sulfur or silicon. Thus, the term $(C_2-C_8)$heteroalkyl refers to a group having from 2 to 8 main chain atoms, at least one of which is a heteroatom. For example, a $C_3$ heteroalkyl group is meant to include $—CH_2OCH_3$ (the oxygen atom taking the place of the central carbon atom in a $C_3$ alkyl propyl) group. A heteroalkyl may be optionally substituted.

The term "heteroaryl" as used herein refers to an aryl radical having from 1 to 4 heteroatoms as ring atoms in the aromatic ring, with the remainder of the ring atoms being carbon atoms. Suitable heteroatoms include oxygen, sulfur, and nitrogen. By way of example only, suitable heteroaryl groups include furanyl, thienyl, pyridyl, pyrrolyl, N-lower alkyl pyrrolyl, pyridyl-N-oxide, pyrimidyl, pyrazinyl, and imidazolyl. A heteroaryl may be optionally substituted.

The term "biaryl" as used herein refers to an aryl radical containing more than one aromatic ring including both fused ring systems and aryl groups substituted with other aryl groups. By way of example only, suitable biaryls include naphthyl and biphenyl. A biaryl may be optionally substituted.

The term "alicyclic" as used herein refers to a moiety or a compound which combines the structural properties of aliphatic and cyclic or heterocyclic compounds and includes, but is not limited to, aromatic, cycloalkyl and bridged cycloalkyl compounds. An alicyclic may be optionally substituted. By way of example only, suitable alicyclics include cyclohexenylethyl and cyclohexylethyl are suitable alicyclic groups.

The term "aralkyl" refers to an alkyl group substituted with an aryl group. Suitable aralkyl groups include benzyl, picolyl, and the like, and may be optionally substituted.

The terms "arylamino" (a), and "aralkylamino" (b), respectively, refer to the group —NRR' wherein respectively, (a) R is aryl and R' is hydrogen, alkyl, aralkyl or aryl, and (b) R is aralkyl and R' is hydrogen or aralkyl, aryl, alkyl.

The term "acyl" refers to —C(O)R where R is alkyl and aryl. By way of example only, acyl radicals include acetyl, pentanoyl, benzoyl, 4-hydroxybenzoyl, pivaloyl and 4-hydroxyphenylacetyl.

The term "carboxy esters" refers to —C(O)OR where R is alkyl, aryl, aralkyl, and alicyclic, all optionally substituted.

The term "carboxyl" refers to —C(O)OH.

The term "oxo" refers to =O attached to carbon or hetero atom.

The term "amino" refers to —NRR' where R and R' are independently selected from hydrogen, alkyl, aryl, aralkyl and alicyclic, all except H are optionally substituted; and R and R' can form a cyclic ring system.

The term "halogen" or "halo" refers to —F, —Cl, —Br and —I.

The term "heterocyclic" and "heterocyclic alkyl" refer to cyclic groups containing at least one heteroatom. Suitable heteroatoms include oxygen, sulfur, and nitrogen. Heterocyclic groups may be attached through a nitrogen or through a carbon atom in the ring. Suitable heterocyclic groups include pyrrolidinyl, morpholino, morpholinoethyl, and pyridyl.

The term "phosphono" refers to $—PO_3R_2$, where R is selected from the group consisting of —H, alkyl, aryl, aralkyl, and alicyclic.

The term "sulfonyl" refers to $—SO_3R$, where R is H, alkyl, aryl, aralkyl, and alicyclic.

The term "acyloxy" refers to the ester group —O—C(O)R, where R is H, alkyl, alkenyl, alkynyl, aryl, aralkyl, or alicyclic.

The term "hydroxy" refers to the OH group

The term "thiol" refers to the SH group.

The term "alkylamino" refers to an amine-$NR_2$ wherein at least one R is an alkyl group.

The term "$(C_1-C_8)$alkylamino" refers to an alkylamino group having a single alkyl group, wherein the alkyl group has up to and including 8 carbon atoms. Suitable alkyl groups may be straight chain, branched, or cyclic and may be optionally substituted.

The term "dialkylamino" refers to an amine-$NR_2$ wherein both R groups are alkyl groups. Suitable alkyl groups may be straight chain, branched, or cyclic and may be optionally substituted.

The term "di($C_1$-$C_8$)alkylamino" refers to an amine-$NR_2$ wherein both R groups are alkyl groups. Suitable alkyl groups may be straight chain, branched, or cyclic and may be optionally substituted. Further, the two alkyl groups may be joined to form a ring comprising the nitrogen as a hetero atom.

The term "aminoalkyl-" refers to the group $NR_2$-alk- wherein "alk" is an alkylene group and R is selected from H, alkyl, aryl, aralkyl, and alicyclic.

The term "alkylaminoalkyl-" refers to the group alkyl-NR-alk- wherein "alk" is an alkylene group and R is H or lower alkyl. "Lower alkylaminoalkyl-" refers to groups where each alkyl group is lower alkyl.

The term "arylaminoalkyl-" refers to the group aryl-NR-alk- wherein "alk" is an alkylene and R is H, alkyl, aryl, aralkyl, and alicyclic. In "lower arylaminoalkyl-", the alkyl group is lower alkyl.

The term "alkylaminoaryl-" refers to the group alkyl-NR-aryl- wherein "aryl" is a divalent group and R is H, alkyl, aralkyl, and alicyclic. In "lower alkylaminoaryl-", the alkyl group is lower alkyl.

The term "alkyloxyaryl-" refers to the group alkyl-O-aryl- wherein an "aryl" is a divalent group. In "lower alkyloxyaryl-", the alkyl group is lower alkyl.

The term "aryloxyalkyl-" refers to an alkylene group substituted with an aryloxy group.

The term "alkoxy" refers to an alkyl group as described above which also bears an oxygen substituent which is capable of covalent attachment to another hydrocarbon radical (such as, for example, methoxy, ethoxy and t-butoxy).

The term ($C_1$-$C_8$)alkoxy as used herein refers to an alkoxy group, wherein alkyl is a ($C_1$-$C_8$)alkyl.

The term "alkenyloxy" as used herein refers to the group —O-alkenyl wherein "alkenyl" is an alkenyl group.

The term ($C_1$-$C_8$)alkenyloxy as used herein refers to alkenyloxy, wherein the alkenyl is a ($C_1$-$C_8$)alkenyl.

The term "aryloxy" as used herein refers to the group Ar—O— wherein "Ar" is an aryl group.

The terms "alkylthio-" as used herein refers to the group alkyl-S—.

The term "($C_1$-$C_8$)alkylthio" as used herein refers to the group alkyl-S— wherein alkyl has up to and including 8 carbon atoms.

The terms "amido" or "carboxamido" as used herein refers to $NR_2$—C(O)— and RC(O)—$NR^1$—, where R and $R^1$ include H, alkyl, aryl, aralkyl, and alicyclic. The term does not include urea, —NR—C(O)—NR—.

The term "aminocarboxamidoalkyl-" as used herein refers to the group $NR_2$—C(O)—N(R)-alk- wherein R includes H, alkyl, aryl, aralkyl, and alicyclic, and "alk" is an alkylene group. "Lower aminocarboxamidoalkyl-" refers to such groups wherein "alk" is lower alkylene.

The term "heteroarylalkyl" refers to an alkyl group substituted with a heteroaryl group.

The term "perhalo" as used herein refers to groups wherein every C—H bond has been replaced with a C-halo bond. Suitable perhaloalkyl groups include —$CF_3$ and —$CFCl_2$. Suitable perhaloalkylene groups include —$CF_2$ and mixed halogen species, e.g., —CFCl.

The term "cyano" or "nitrile" as used herein refers to a —C≡N group.

The term "nitro" as used herein refers to a —$NO_2$ group.

The term "alkylsulfonyl" as used herein refers alkOS$(O)_2$— wherein alk is an alkyl.

The term "phosphonate" as used herein refers to the moiety P(=O)(OR)$_2$ wherein P(=O) designates a phosphorous oxo group, an wherein R may be an aliphatic group.

The term "ester" as used herein refers to a chemical moiety with formula —(R)$_n$COOR', where R and R' are independently selected from the group consisting of alkyl or aryl and n is 0 or 1.

The term "amide" as used herein refers to a chemical moiety with formula —(R)$_n$—CONHR', where R and R' are independently selected from the group consisting of alkyl or aryl and n is 0 or 1.

The term "imide" as used herein refers to a chemical moiety with formula —(R)$_n$—CONR$_2$', where R and R' are independently selected from the group consisting of alkyl or aryl and n is 0 or 1.

The term "cross-coupling" as used herein refers a reaction between an electrophile and a nucleophile resulting in the formation of a new covalent carbon-carbon bond.

The term "organostannane" or "organostannane compound" as used herein refers to a compound comprising at least one Sn—R chemical bond, wherein R is an organic moiety. Preferably R can be either an alkyl, alkenyl, aryl, heteroaryl, allyl or alkynyl moiety. Preferred organostannanes are any which can engage in cross-coupling reactions.

The term "organozinc" or "organozinc compound" as used herein refers to a compound having at least one Zn—R chemical bond, wherein R is an organic moiety. Preferably R can be either an alkyl, alkenyl, aryl, heteroaryl, allyl or alkynyl moiety. Preferred organozinc compounds according to the present invention are those which engage in cross-coupling reactions.

The term "organoboron" or "organoboron compound" as used herein refers to a compound comprising at least one B—R chemical bond, wherein R is an organic moiety. Preferably R can be either an alkyl, alkenyl, aryl, heteroaryl, allyl or alkynyl moiety. Preferred organoborons are those which engage in cross-coupling reactions.

The term "organoaluminum" or "organoaluminum compound" as used herein refers to a compound comprising at least one Al—R chemical bond, wherein R is an organic moiety. Preferably R can be either an alkyl, alkenyl, aryl, heteroaryl, allyl or alkynyl moiety. Preferred organoaluminums are those which engage in cross-coupling reactions.

The term "organomagnesium", "organomagnesium compound", "organomagnesium reagent" or "Grignard reagent" as used herein refers to a compound comprising at least one Mg—R chemical bond, wherein R is an organic moiety. Preferably R can be either an alkyl, alkenyl, aryl, heteroaryl, allyl or alkynyl moiety. Preferred organomagnesium compounds are those which engage in cross-coupling reactions The term "organolithium" or "organolithium compound" as used herein refers to a compound comprising at least one Li—R chemical bond, wherein R is an organic moiety. Preferably R can be either an alkyl, alkenyl, aryl, heteroaryl, allyl or alkynyl moiety.

The term "organosilicon" or "organosilicon reagent" as used herein refers to a compound comprising at least one Si—R chemical bond, wherein R is an organic moiety. Preferably R can be either an alkyl, alkenyl, aryl, heteroaryl, allyl or alkynyl moiety.

The term "organocopper reagent" also know as "organocuprates" as used herein refers to a compound comprising at least one Cu—R chemical bond, wherein R is an organic moiety. Preferably R can be either an alkyl, alkenyl, aryl, heteroaryl, allyl or allynyl moiety.

The term dialkylphosphite, refers to compound having a formula: $R_2P(=)OR'$ wherein R and R' comprise aliphatic or aryl groups. Preferably R and R' are independently selected from the group consisting of an alkyl, alkenyl, aryl, heteroaryl, allyl or alkynyl moiety.

The term "aryl boronic acid" as used herein refers to compounds having a formula: $ArB(OH)_2$, wherein Ar refers to an aryl.

The term "metal halide" as used herein refers to any covalently or ionically bonded compound comprising at least one electropositive element and at least one electro-negative element. According to one aspect of the present invention, a metal halide is a source of a halide anion.

The term "addition of a transition metal catalyst" refers to the use of a transition metal catalyst to promote a desired chemical transformation. A transition metal catalyst comprises at least one transition metal and associated ligands. A non-catalytic or poorly catalytic transition metal can often be converted to a transition metal catalyst by the addition of ligands into the reaction mixture; such ligands include, by way of example only, trialkylphosphines, triarylphosphines, and bis(diarylphosphino)L compounds, wherein L can be an alkylene, divalent aryl, divalent alkenyl, divalent alkynyl, divalent heteroalkyl, divalent heteroaryl, or a derivative of ferrocene. In one set of embodiments, ligands include 1,3-bis (diphenylphosphino)propane or 1,1'-bis(diphenylphosphanyl)ferrocene. Any particular transition metal catalyst may have multiple ligands, not all of which need to be identical. In one embodiment, the transition metal is palladium. The new catalytically active species are also known as transition metal complexes. The skilled artisan will understand that the examples provided herein for transition metal catalyst, transition metal and ligand are for illustrative purposes only and that the scope of the present invention is not limited by the identity of the transition metal catalyst, the transition metal, and the ligands. The catalyst and the optional ligand which together form a catalytically active species may be used at levels close to 100% relative to the reacting species, preferably <25% relative to the reacting species, more preferably <10% relative to the reacting species.

The term "covalently attached" as used herein refers to the presence of a covalent bond between two or more moieties.

The term "nucleophile" as used herein is a compound or moiety that is reactive towards an electrophile so as to form a covalent between the nucleophile and electrophile. The terms "nucleophile" and "electrophile" have their usual meanings familiar to synthetic and/or physical organic chemistry. Carbon electrophiles typically comprise one or more alkyl, alkenyl, alkynyl or aromatic carbon atom substituted with any atom or group having a Pauling electronegativity greater than that of hydrogen. Examples of preferred carbon electrophiles include but are not limited to carbonyls (especially aldehydes and ketones), oximes, hydrazones, epoxides, aziridines, alkyl-, alkenyl-, and aryl halides, acyls, sulfonates, and perhalosulfonates. Other examples of carbon electrophiles include unsaturated carbons electronically conjugated with electron-withdrawing groups, examples being the β-carbon in α,β-unsaturated ketones or carbon atoms in fluorine substituted aryl groups. The skilled artisan will realize that the scope of the invention is not limited by the identity of the nucleophile.

The term "activated complex" as used herein refers to a moiety that is covalently bound to a surface-bound activator and which, as a result, has an increased chemical reactivity relative to its parent compound. According to one embodiment of the present invention an aryl alcohol compound is converted into a more reactive, surface-bound aryloxy moiety, i.e., an activated complex, upon reaction with a surface-bound activator of the present invention.

The term "hydride" or "hydride reagent" as used herein, refers to proton that can act as a nucleophile. Examples of hydride reagents familiar to the skilled artisan include but are not limited to $NaBH_4$, $LiAlH_4$, as well as any suitable transition-metal hydride. The hydride may also be formed in situ, or during the course of the reaction, by an interaction between one or more reagents. By way of example only, a transition metal-hydride is formed in situ in the presence of $Pd(OAc)_2$, ligand and formic acid, as described in Example 3 below.

The term "enolizable ketone" refers to any ketone bearing a hydrogen on an "alpha carbon" (the carbon atom once removed from that bearing the oxo group), wherein said alpha proton may be readily removed by exogenous base or via intra molecular tautomerization:

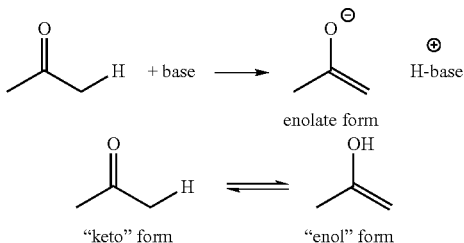

The term "compound" as used herein refers to any identifiable molecule.

The term "conditions" refers to factors that can affect the outcome of a particular reaction and which can be controlled by the operator performing the reaction or sequence of reactions. Examples of such conditions include but are not limited to the length of time that a set of reagents is allowed to interact with a substrate, the temperature, the solvent, the rates of addition of particular reagents, and the like. The skilled artisan will recognize that each particular set of reagents may have its own optimal set of "conditions".

The term "conditions sufficient" as used herein refers to those conditions that are adequate to produce the results desired.

The term "contacting" as used herein refers to any process whereby any reagent or combinations thereof is mixed, stirred, added to, shaken, dissolved, passed-over, passed through, another said reagent under conditions such that two or more reagents can undergo a chemical reaction or transformation.

The term "reagent" as used herein refers to any chemical compound used alone or in combination with a different chemical compound to produce a desired chemical reaction. The term "reagent" includes all catalysts (transition metal based or otherwise), ligands, acids, bases and other materials that are added to a reaction mixture in order to provide the desired result.

The term "moiety" as used herein refers to a specific portion of a molecule, usually complex, that has a characteristic chemical or property or reactivity.

The term "linking group" as used herein refers to the entire chain of atoms liking an activator portion with a solid or semi-solid support.

General

The present invention provides a variety of reagents, particularly support-bound activators, that have utility in the area of combinatorial synthesis. Each reagent includes an activator portion that serves as a reactive center and a linking group component that serves to provide a robust linkage between the support and the activator portion. The linking group components further include an activator enhancing portion that serves to increase the reactivity of the activator portion and suitable spacer that provides sufficient distance between the activator portion and the support. The present invention also provides for activated supports on which construction of a target or library of targets takes place; the targets can also be cleaved from the activated support to liberate the desired compound from the activated support.

One important aspect of the present invention is the use of the activated supports described herein as traceless linkers, as that term is understood by those skilled in the art. As described above, the term "traceless linker" has been used to describe a strategy of releasing compounds from a solid support with little or no trace of the original point of attachment. See James, *Tetrahedron Lett.*, 1999, 55, 4855; Andres, et al., *Curr. Opin. Chem. Biol.*, 1998, 2, 353; Reitz, *Curr. Opin. Drug Discovery Dev.*, 1999, 2, 358; and Zaragoza, *Angew. Chem., Int. Ed.* 2000, 39, 2077. As demonstrated in Examples 3, 4 and 5, and in Tables 1, 2, and 3, the activated supports of the present invention will have wide utility as traceless linkers in solid phase organic chemistry. As one skilled in the art will realize, these examples are merely illustrative and the activated supports of the present invention are fully expected to act as traceless linkers in any reaction that can cleave a triflate-carbon bond.

In addition, any of the reactions described herein, as well as any reaction known in the art of organic chemistry that can retain the integrity of a triflate-carbon bond, can be used to construct either a target or a library of targets on the activated supports of the present invention. Accordingly a preferred aspect of the present invention is a support-activated target group. In addition, another preferred aspect of the present invention is a library of support-activated target groups.

The support-bound activators or the present invention also serve to activate certain centers toward such reactions as reductions, Suzuki couplings, Stille couplings, Heck couplings, Buchwald reactions, CO insertions, CN insertions, carbon-sulfur bond formation, and others.

The use of triflates and nonaflates as precursors for aryl and vinyl cations has been widely recognized. See, for example, Ritter, *Synthesis*, 8:735-762 (1993). Briefly, an oxygen atom on an aryl or vinyl group (e.g., as a phenol or an enolizable ketone) can be activated as a triflate ester (trifluoromethane sulfonate ester) or a related nonaflate ester towards a subsequent reduction or cross-coupling that gives rise to a variety of substituted aromatic compounds or olefinic compounds.

It would be desirable to conduct the perfluorosulfonyl-directed transformations on solid phase and take advantage of the versatile synthetic transformations known for vinyl and aryl triflates (see, Ritter, ibid.). For example, the reductive cleavage of a polymer-supported aryl triflate could lead to deoxygenation of phenols without leaving a trace of the phenolic hydroxy group as a point of attachment to the polymer, or resin. Wustrow and coworkers (*Tetrahedron Lett.* 39:3651 (1998)) reported the reductive cleavage of electron poor arylsulfonates from an ion-exchange resin based sulfonyl linker under stringent cleavage conditions (140° C. for 12 h), but to date, there have been no reports of polymer-supported triflates and nonaflates that could be used for activating hydroxy groups toward a variety of synthetic transformations.

NAFION™ resin is well known, yet suffers from having poor swelling properties and is difficult to activate. The inability of NAFION™ to swell in the presence of common organic solvents prevents the vast majority of surface-bound reactive groups from reacting with compounds in solution. As a result, NAFION™ has not found much utility in solid-phase organic synthesis or in other uses that require more than a catalytic amount of available surface-bound reactive groups.

What is needed in the art are support-bound activators that have improved swelling properties and that are able to participate in perfluorosulfonate-based activation/displacement chemistry. Such support-bound activators and the related activated supports are provided below.

The present invention also provides for strongly acidic supports which find application as catalysts or scavenger resins, particularly those having increased swelling properties. In addition, the present invention provides for silylating supports which find application in analytical chemistry or in other areas in which a silylated compound is desired.

DESCRIPTION OF THE EMBODIMENTS

Support-Bound Activators

In one aspect, the present invention provides a support-bound activator having the formula:

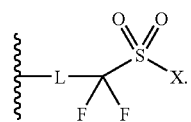

(I)

In formula I, the letter L represents a linking group component; the letter X represents F, Cl, trisubstituted silyloxy or OH. The support-bound activator is attached to a solid or semi-solid support by at least one covalent bond.

Turning first to the solid or semi-solid support, the present invention is useful in a variety of solid-phase synthesis applications and, accordingly, a variety of supports find utility in this any other aspects of the invention. Typical solid supports include, but are not limited to, cross-linked divinylbenzene-styrene (polystyrene), controlled pore glass (CPG), polyacrylamides, poly(ethyleneglycol)monomethyl ether and poly (ethylene glycol) (PEG), silica gel, cellulose, acrylic acid grafted polypropylene, and the like. Additionally, the solid support contains a reactive moiety suitable for attaching the linking group component. Suitably reactive moieties include, for example, a carboxylic acid, alcohol, amine, halomethyl and the like which is used to covalently attach the linking group component during construction of the present support-bound activators. Many of these supports are available as functional polymers having reactive groups. Examples of such supports, include, by way of example, Acryloyl Wang resin, REM resin, Vinyl polystyrene, Vinylsulfonylmethyl polystyrene, (3-Formylindolyl)acetamidomethyl polystyrene, 2-(3,5-Dimethoxy-4-formylphenoxy)ethoxymethyl polystyrene, 2-(4-Formyl-3-methoxyphenoxy)ethyl polystyrene, 4-(4-Formyl-3-methoxyphenoxy)butyryl AM resin, 4-Benzyloxybenzaldehyde polystyrene, Aldehyde Wang resin, Formylpolystyrene, 1% DVB, NovaSyn® TG acetal resin, Polystyrene-CHO, Carboxypolystyrene, NovaSyn® TG carboxy resin, Polystyrene-COOH, 4-(2',4'-Dimethoxyphenyl-Fmoc-aminomethyl)-phenoxy resin, 4-Methylbenzhydrylamine resin HCl, 4-Methylbenzhydrylamine resin HCl, 9-Fmoc-amino-xanthen-3-yloxy, 9-Fmoc-amino-xanthen-3-yloxy, Amino-(4-methoxyphenyl)methyl polystyrene, Ethylamino-xanthen-3-yloxy-Merrifield resin, NovaSyn® TG Sieber resin, NovaSyn® TGR resin, Rink Amide AM resin, Rink Amide MBHA resin, Rink amide NovaGel™, Rink amide PEGA resin, Rink Amide resin, Sieber Amide resin, Sieber Ethylamide resin, Amino methyl resin, Amino PEGA resin, Aminomethyl NovaGel™, Aminomethylated polystyrene, N-Methylaminomethyl polystyrene, 4-Fmoc-hydrazinobenzoyl AM resin, 1H-Benzotriazole polystyrene, Benzotriazole-5-carbamidomethyl polystyrene, N-Fmoc-N-methoxy-β-alanine AM resin, Weinreb AM resin, 4-Sulfamylbenzoyl AM resin, (±)-1-(2,3-Isopropylidene)glycerol polystyrene, (±)-2,2-Dimethyldioxolan-4-methoxymethyl polystyrene, (±)-1-Glycerol polystyrene, 4-(2',4'-Dimethoxyphenyl-hydroxymethyl)-phenoxy resin, 4-(2',4'-Dimethoxyphenyl-hydroxymethyl)-phenoxy resin, 4-(2',4'-Dimethoxyphenyl-hydroxymethyl)-phenoxy resin, 4-Hydroxymethyl-3-methoxyphenoxybutyric acid AM resin, 4-Hydroxymethyl-3-methoxyphenoxybutyric acid BHA resin, 4-Hydroxymethyl-3-methoxyphenoxybutyric acid MBHA resin, 4-Hydroxymethylphenoxyacetyl NovaGel™, 4-Hydroxymethylphenoxyacetyl PEGA resin, HMP resin, HMPA-NovaGel™, HMPB-AM resin, HMPB-BHA resin, HMPB-MBHA resin, Hydroxy-(2-chlorophenyl)methyl polystyrene, Hydroxymethylpolystyrene, NovaSyn® TG HMP resin, p-Benzyloxybenzyl Alcohol resin, Polystyrene-CH$_2$OH, Rink Acid resin, Trichloroacetimidate Wang resin, Wang resin, 4-Hydroxymethylbenzoic acid AM resin, 4-Hydroxymethylbenzoic acid NovaGel™, 4-Hydroxymethyl-benzoic acid PEGA resin, 4-Hydroxyphenylsulfanylmethyl polystyrene, 9-(Hydroxymethyl)fluorene-4-carboxamidomethyl polystyrene, HESM polystyrene, HMBA-AM resin, HMBA-NovaGel™, HMBA-PEGA resin, Hydroxyethylsulfanylmethyl polystyrene, NovaSyn® TG HMBA resin, NovaSyn® TG hydroxy resin, Oxime resin, Aminoethyl photolinker resin, Hydroxyethyl photolinker resins, Hydroxymethyl photolinker resins, 3-[4-(Tritylmercapto)phenyl]propionyl AM resin, Mercaptomethyl polystyrene, NovaSyn® TG tritylthiol resin, Thiol 2-chlorotrityl resin, Thiol 4-methoxytrityl resin, (4-Bromophenyl)diisopropylsilyloxymethyl polystyrene, (4-Formylphenyl)diisopropylsilyloxymethyl polystyrene, (4-Trityloxyphenyl)diisopropylsilyloxymethyl polystyrene. Solid supports also include TENTAGEL™, HYPOGEL™, JANDAJEL™, AND ARGOGEL™. Other solid supports include PEGylated polystyrene (polystyrene derivatized with polyethylene glycol), Tentagel-NH$_2$ resin, and derivatized Tentagel-NH$_2$ resin (e.g., by treatment with acetyl chloride followed by reduction with LiAlH$_4$ to provide Tentagel-NHEt resin). See also the Novabiochem Catalogue 2000 for additional resins and immobilized functional groups.

Such supports may take any size, shape or form, including particulate and non-particulate forms or shapes, spheres, disks, pellets, sheets, plugs, pins, crowns, lanterns, in beaded and non-beaded forms, resins, gels, microspheres, as well as amorphous forms and shapes. Embodiments of particulate supports, include beads, pellets, disks, amorphous particles, or other conventional forms. The solid or semi-solid supports may be used as single particle, as groups of particles, as free flowing particles, and may be packed into columns, tubes or other flow-through devices. In a one embodiment, the diameter of the particulate support is 20-2000 micron, preferably 75-500 micron, more preferably 100-200 micron. As one skilled in the art will readily recognize, the scope of the present invention is not limited to the size, form, or shape of the solid or semi-solid support.

The linking group component can have a variety of structures. The linking group component is one which provides suitable spacing for the activator portion (—CF$_2$—SO$_2$—X) to interact freely with molecules or reactive components exposed to the activator portion. The linking group component is preferably 6-50 atoms long, more preferably 8-40 atoms long, even more preferably 8-30 atoms long, and yet more preferably 8-20 atoms long, thus providing sufficient exposure for the attached activator portion. Additionally, the linking group component, prior to attachment to the support, will have a attaching portion and a longer chain portion. The attaching portion is that part of the linking group component which can be directly attached to the solid support. This portion can be attached to the solid support via carbon-carbon bonds using, for example, supports having exposed (poly) trifluorochloroethylene moieties, or preferably, by siloxane bonds (using, for example, glass or silicon oxide as the solid support). Siloxane bonds the support are formed in one embodiment via reactions of attaching portions bearing trichlorosilyl or trialkoxysilyl groups. The attaching groups will also have a site for attachment of the longer chain portion. For example, groups which are suitable for attachment to a longer chain portion would include amines, hydroxyl, thiol, and carboxyl.

One skilled in the art will recognize that many additional methods of attaching linkers to solid and semi-solid supports exist. One method uses an amino resin to which an acid-bearing linker is attached via conventional techniques. Another method is the use of aryl ether linkages by coupling a phenol to a Merrifield (or equivalent) resin.

The longer chain portion can be any of a variety of molecules which are inert to the subsequent conditions used in the activator reactions described in further detail below. These longer chain portions can be ethylene glycol oligomers containing 2-14 monomer units, or more preferably 2-10 monomer units, and even more preferably 2-8 monomer units; in addition, the longer chain portions can be diamines, diacids, amino acids, peptides, or combinations thereof. In some embodiments, the longer chain portion also comprises an activator enhancing portion, i.e., a portion that increases the reactivity of the activator relative to an alkylene or ethylene glycol linking group. More particularly, an activator enhancing portion is one that provides additional electron withdrawing character to the activator portion (e.g., the —CF$_2$—SO$_2$—X portion).

In one group of embodiments, X is a member selected from the group consisting of F and Cl. In another group of embodiments, L comprises an activator enhancing portion selected from the group consisting of:

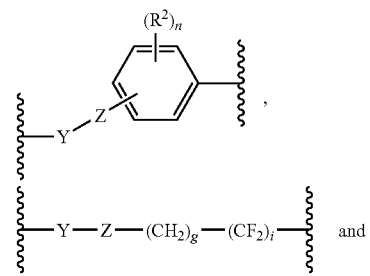

-continued

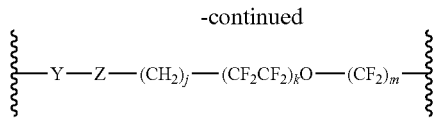

wherein Y is a member selected from the group consisting of a chemical bond, O, CO, S, and $NR^1$; Z is a member selected from the group consisting of a chemical bond or CO; $R^1$ is a member selected from the group consisting of H and $(C_1-C_8)$ alkyl; each $R^2$ is independently a member selected from the group consisting of hydrogen, halogen, $(C_1-C_8)$alkyl, $(C_1-C_8)$alkoxy, $(C_2-C_8)$heteroalkyl, $(C_1-C_8)$alkylthio, $(C_1-C_8)$alkylamino, di$(C_1-C_8)$alkylamino, cyano, nitro and $(C_1-C_8)$alkylsulfonyl; the subscript 'g' is an integer selected from the group consisting of 0, 1, 2, 3, 4, 5, 6, 7, 8, 9, and 10; the subscript 'i' is an integer selected from the group consisting of 1, 2, 3, 4, 5, and 6; the subscript 'j' is an integer selected from the group consisting of 0, 1, 2, 3, 4, 5, 6, 7, 8, 9, and 10; the subscript 'k' is an integer selected from the group consisting of 1, 2, 3, and 4; the subscript 'm' is an integer selected from the group consisting of 2 and 3; and the subscript 'n' is an integer selected from the group consisting of 0, 1, 2, 3, and 4. In the groups described herein as dialkylamino, the alkyl groups can be the same or different, or can optionally be combined to form a ring having additional heteroatoms (e.g., pyrrolidino, morpholino, piperazino).

In another embodiment, the support-bound activator is available in kit form for use in solid phase organic chemistry, as a reagent or catalyst in solution phase organic chemistry, as a scavenger resin in solution phase organic chemistry, as a silylating agent for use in analytical chemistry, and in particular, in chromatography, and as a reagent for the production of PET-ready molecules.

In one group of embodiments, the support-bound activators of the present invention are:

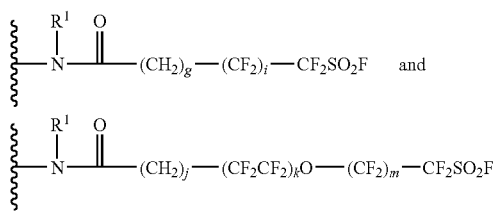

wherein the symbol $R^1$ and the subscripts g, i, j, k and m all have the meanings provided above.

In another group of embodiments, the support-bound activators have a formula selected from:

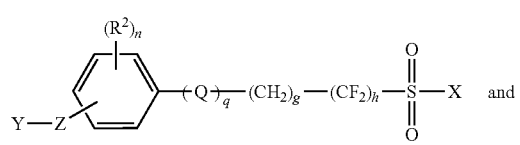

A

-continued

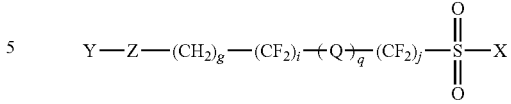

B

In each of formulae A and B, X can be F, Cl, trisubstituted silyloxy, or OH; Q is O; Z is a chemical bond or C=O; Y is O-support or $NR_1$-support wherein $R_1$ is H, $(C_1-C_8)$alkyl or aryl and the support is a PEG-modified polystyrene or a Merrifield resin; and each $R^2$ is as defined more generally above. The subscripts in formulae A and B are as follows: 'g' is an integer selected from the group consisting of 0, 1, 2, 3, 4, 5, 6, 7, 8, 9, 10, and 11; 'h' is an integer selected from the group consisting of 1, 2, 3, 4, 5, 6, 7, and 8; 'i' is an integer selected from the group consisting of 0, 1, 2, 3, 4, 5, 6, 7, and 8; 'j' is an integer selected from the group consisting of 1, 2, 3, and 4; 'k' is an integer selected from the group consisting of 1, 2, 3, and 4; 'm' is an integer selected from the group consisting of 2 and 3; 'n' is an integer selected from the group consisting of 0, 1, 2, 3, and 4; and 'q' is an integer selected from the group consisting of 1, and 2.

In one particular embodiment in formulae A and B, X is F; Q is O; Z is C=O, Y is NH-support wherein the support is a PEG-modified polystyrene; and each $R^2$ is H.

Activated Supports

In another aspect, the present invention provides an activated support comprising a solid or semi-solid support; and at least one support-bound activator having the formula:

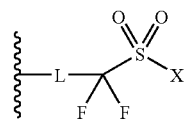

wherein L is a linking group component; X is a member selected from the group consisting of F, Cl, OH, and trisubstituted silyloxy; and wherein the support-bound activator is covalently attached to the solid or semi-solid support.

Turning first to the solid or semi-solid support, the present invention is useful in a variety of solid-phase synthesis applications and, accordingly, a variety of supports find utility in this aspect of the invention. Typical solid supports include, but are not limited to, cross-linked divinylbenzene-styrene (polystyrene), controlled pore glass (CPG), polyacrylamides, poly(ethyleneglycol)monomethyl ether and poly(ethylene glycol) (PEG), silica gel, cellulose, acrylic acid grafted polypropylene, and the like. Additionally, the solid support contains a reactive moiety suitable for attaching the linking group component. Suitably reactive moieties include, for example, a carboxylic acid, alcohol, amine, halomethyl and the like which is used to covalently attach the linking group component during construction of the present support-bound activators. Many of these supports are available as functional polymers having reactive groups. Examples of such supports, include, by way of example, Acryloyl Wang resin, REM resin, Vinyl polystyrene, Vinylsulfonylmethyl polystyrene, (3-Formylindolyl)acetamidomethyl polystyrene, 2-(3,5-Dimethoxy-4-formylphenoxy)ethoxymethyl polystyrene, 2-(4-Formyl-3-methoxyphenoxy)ethyl polystyrene, 4-(4-Formyl-3-methoxyphenoxy)butyryl AM resin, 4-Benzyloxybenzaldehyde polystyrene, Aldehyde Wang resin, Formylpolystyrene, 1% DVB, NovaSyn® TG acetal resin, Polystyrene-CHO, Carboxypolystyrene, NovaSyn® TG carboxy resin, Polystyrene-COOH, 4-(2',4'-Dimethoxyphenyl-Fmoc-aminomethyl)-phenoxy resin, 4-Methylbenzhydrylamine resin HCl, 4-Methylbenzhydrylamine resin HCl, 9-Fmoc-amino-xanthen-3-yloxy, 9-Fmoc-amino-xanthen-3-yloxy, Amino-(4-methoxyphenyl)methyl polystyrene, Ethylamino-xanthen-3-yloxy-Merrifield resin, NovaSyn® TG Sieber resin, NovaSyn® TGR resin, Rink Amide AM resin, Rink Amide MBHA resin, Rink amide NovaGel™, Rink amide PEGA resin, Rink Amide resin, Sieber Amide resin, Sieber Ethylamide resin, Amino methyl resin, Amino PEGA resin, Aminomethyl NovaGel™, Aminomethylated polystyrene, N-Methylaminomethyl polystyrene, 4-Fmoc-hydrazinobenzoyl AM resin, 1H-Benzotriazole polystyrene, Benzotriazole-5-carbamidomethyl polystyrene, N-Fmoc-N-methoxy-β-alanine AM resin, Weinreb AM resin, 4-Sulfamylbenzoyl AM resin, (±)-1-(2,3-Isopropylidene) glycerol polystyrene, (±)-2,2-Dimethyldioxolan-4-methoxymethyl polystyrene, (±)-1-Glycerol polystyrene, 4-(2',4'-Dimethoxyphenyl-hydroxymethyl)-phenoxy resin, 4-(2',4'-Dimethoxyphenyl-hydroxymethyl)-phenoxy resin, 4-(2',4'-Dimethoxyphenylhydroxymethyl)-phenoxy resin, 4-Hydroxymethyl-3-methoxyphenoxybutyric acid AM resin, 4-Hydroxymethyl-3-methoxyphenoxybutyric acid BHA resin, 4-Hydroxymethyl-3-methoxyphenoxybutyric acid MBHA resin, 4-Hydroxymethylphenoxyacetyl NovaGel™, 4-Hydroxymethylphenoxyacetyl PEGA resin, HMP resin, HMPA-NovaGel™, HMPB-AM resin, HMPB-BHA resin, HMPB-MBHA resin, Hydroxy-(2-chlorophenyl)methyl polystyrene, Hydroxymethylpolystyrene, NovaSyn® TG HMP resin, p-Benzyloxybenzyl Alcohol resin, Polystyrene-$CH_2OH$, Rink Acid resin, Trichloroacetimidate Wang resin, Wang resin, 4-Hydroxymethylbenzoic acid AM resin, 4-Hydroxymethylbenzoic acid NovaGel™, 4-Hydroxymethylbenzoic acid PEGA resin, 4-Hydroxyphenylsulfanylmethyl polystyrene, 9-(Hydroxymethyl)fluorene-4-carboxamidomethyl polystyrene, HESM polystyrene, HMBA-AM resin, HMBA-NovaGel™, HMBA-PEGA resin, Hydroxyethylsulfanylmethyl polystyrene, NovaSyn® TG HMBA resin, NovaSyn® TG hydroxy resin, Oxime resin, Aminoethyl photolinker resin, Hydroxyethyl photolinker resins, Hydroxymethyl photolinker resins, 3-[4-(Tritylmercapto)phenyl]propionyl AM resin, Mercaptomethyl polystyrene, NovaSyn® TG tritylthiol resin, Thiol 2-chlorotrityl resin, Thiol 4-methoxytrityl resin, (4-Bromophenyl)diisopropylsilyloxymethyl polystyrene, (4-Formylphenyl)diisopropylsilyloxymethyl polystyrene, (4-Trityloxyphenyl)diisopropylsilyloxymethyl polystyrene. Solid supports also include TENTAGEL™, HYPOGEL™, JANDAJEL™, AND ARGOGEL™. Other solid supports include PEGylated polystyrene (polystyrene derivatized with polyethylene glycol), Tentagel-$NH_2$ resin, and derivatized Tentagel-$NH_2$ resin (e.g., by treatment with acetyl chloride followed by reduction with $LiAlH_4$ to provide Tentagel-NHEt resin). See also the Novabiochem Catalogue 2000 for additional resins and immobilized functional groups.

Such supports may take any size, shape or form, including particulate and non-particulate forms or shapes, spheres, disks, pellets, sheets, plugs, pins, crowns, lanterns, in beaded and non-beaded forms, resins, gels, microspheres, as well as amorphous forms and shapes. Embodiments of particulate supports, include beads, pellets, disks, amorphous particles, or other conventional forms. The solid or semi-solid supports may be used as single particle, as groups of particles, as free flowing particles, and may be packed into columns, tubes or other flow-through devices. In a one embodiment, the diameter of the particulate support is 20-2000 micron, preferably 75-500 micron, more preferably 100-200 micron. As one skilled in the art will readily recognize, the scope of the present invention is not limited to the size, form, or shape of the solid or semi-solid support.

The linking group component can have a variety of structures. The linking group component is one which provides suitable spacing for the activator portion (—$CF_2$—$SO_2$—X) to interact freely with molecules or reactive components exposed to the activator portion. The lining group component is preferably 6-50 atoms long, more preferably 8-40 atoms long, even more preferably 8-30 atoms long, and yet more preferably 8-20 atoms long, thus providing sufficient exposure for the attached activator portion. Additionally, the linking group component, prior to attachment to the support, will have a attaching portion and a longer chain portion. The attaching portion is that part of the linking group component which can be directly attached to the solid support. This portion can be attached to the solid support via carbon-carbon bonds using, for example, supports having exposed (poly) trifluorochloroethylene moieties, or preferably, by siloxane bonds (using, for example, glass or silicon oxide as the solid support). Siloxane bonds the support are formed in one embodiment via reactions of attaching portions bearing trichlorosilyl or trialkoxysilyl groups. The attaching groups will also have a site for attachment of the longer chain portion. For example, groups which are suitable for attachment to a longer chain portion would include amines, hydroxyl, thiol, and carboxyl.

One skilled in the art will recognize that many additional methods of attaching linkers to solid and semi-solid supports exist. One method uses an amino resin to which an acid-bearing linker is attached via conventional techniques. Another method is the use of aryl ether linkages by coupling a phenol to a Merrifield (or equivalent) resin.

The longer chain portion can be any of a variety of molecules which are inert to the subsequent conditions used in the activator reactions described in further detail below. These longer chain portions can be ethylene glycol oligomers containing 2-14 monomer units, or more preferably 2-10 monomer units, and even more preferably 2-8 monomer units; in addition, the longer chain portions can be diamines, diacids, amino acids, peptides, or combinations thereof. In some embodiments, the longer chain portion also comprises an activator enhancing portion, i.e., a portion that increases the reactivity of the activator relative to an alkylene or ethylene glycol linking group. More particularly, an activator enhancing portion is one that provides additional electron withdrawing character to the activator portion (e.g., the —$CF_2$—$SO_2$—X portion).

In one group of embodiments, X is a member selected from the group consisting of F and Cl. In another group of embodiments, L comprises an activator enhancing portion selected from the group consisting of:

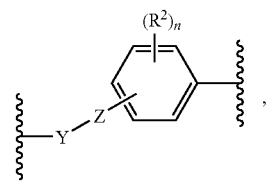

-continued

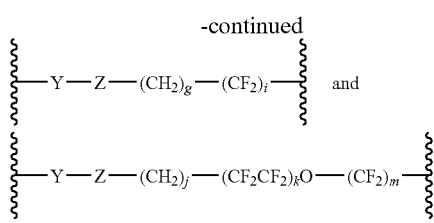

wherein Y is a member selected from the group consisting of a chemical bond, O, CO, S, and $NR^1$; Z is a member selected from the group consisting of a chemical bond or CO; each $R^2$ is independently a member selected from the group consisting of hydrogen, halogen, $(C_1-C_8)$alkyl, $(C_1-C_8)$alkoxy, $(C_2-C_8)$heteroalkyl, $(C_1-C_8)$alkylthio, $(C_1-C_8)$alkylamino, di$(C_1-C_8)$alkylamino, cyano, nitro and $(C_1-C_8)$alkylsulfonyl; the subscript 'g' is an integer selected from the group consisting of 0, 1, 2, 3, 4, 5, 6, 7, 8, 9, and 10; the subscript 'i' is an integer selected from the group consisting of 1, 2, 3, 4, 5, and 6; the subscript 'j' is an integer selected from the group consisting of 0, 1, 2, 3, 4, 5, 6, 7, 8, 9, and 10; the subscript 'k' is an integer selected from the group consisting of 1, 2, 3, and 4; the subscript 'm' is an integer selected from the group consisting of 2 and 3; and the subscript 'n' is an integer selected from the group consisting of 0, 1, 2, 3, and 4. In the groups described herein as dialkylamino, the alkyl groups can be the same or different, or can optionally be combined to form a ring having additional heteroatoms (e.g., pyrrolidino, morpholino, piperazino).

In one group of embodiments, the support-bound activators of the present invention are:

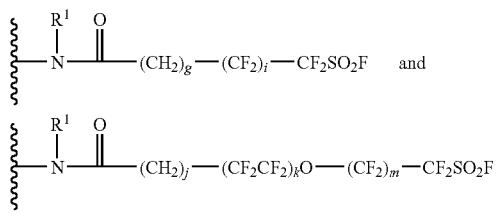

wherein the symbol $R^1$ and the subscripts g, i, j, k and m all have the meanings provided above.

In another group of embodiments, the support-bound activators have a formula selected from:

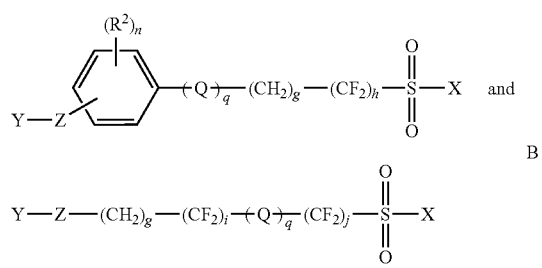

In each of formulae A and B, X can be F, Cl, trisubstituted silyloxy, or OH; Q is O; Z is a chemical bond or C=O; Y is O-support or $NR_1$-support wherein $R_1$ is H, $(C_1-C_8)$alkyl or aryl and the support is a PEG-modified polystyrene or a Merrifield resin; and each $R^2$ is as defined more generally above. The subscripts in formulae A and B are as follows: 'g' is an integer selected from the group consisting of 0, 1, 2, 3, 4, 5, 6, 7, 8, 9, 10, and 11; 'h' is an integer selected from the group consisting of 1, 2, 3, 4, 5, 6, 7, and 8; 'i' is an integer selected from the group consisting of 0, 1, 2, 3, 4, 5, 6, 7, and 8; 'j' is an integer selected from the group consisting of 1, 2, 3, and 4; 'k' is an integer selected from the group consisting of 1, 2, 3, and 4; 'm' is an integer selected from the group consisting of 2 and 3; 'n' is an integer selected from the group consisting of 0, 1, 2, 3, and 4; and 'q' is an integer selected from the group consisting of 1, and 2.

In one particular embodiment in formulae A and B, X is F; Q is O; Z is C=O, Y is NH-support wherein the support is a PEG-modified polystyrene; and each $R^2$ is H.

In still other embodiments, the activated support comprises a plurality of support-bound activators, with a concentration of at least 1 nmol support-bound activators per gram of activated support, more preferably, at least 1 µmol support-bound activators per gram of activated support, and even more preferably, at least 1 mmol support-bound activators per gram of activated support.

In another embodiment, the activated support is available in kit form for use in solid phase organic chemistry, as a reagent or catalyst in solution phase organic chemistry, as a scavenger resin in solution phase organic chemistry, as a silylating agent for use in analytical chemistry, and in particular, in chromatography, and as a reagent for the production of PET-ready molecules.

Support-Activated Targets

In another aspect, the present invention provides a support-activated target comprising a solid or semi-solid support; an activating group covalently attached to the solid or semi-solid support, wherein the activating group has the formula:

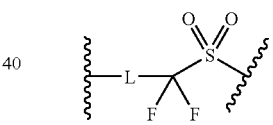

wherein L is an linking group component; and a target group covalently attached to the activating group; wherein the target group can be cleaved from the activating group by a nucleophile.

Turning first to the solid or semi-solid support, the present invention is useful in a variety of solid-phase synthesis applications and, accordingly, a variety of supports find utility in this aspect of the invention. Typical solid supports include, but are not limited to, cross-linked divinylbenzene-styrene (polystyrene), controlled pore glass (CPG), polyacrylamides, poly(ethyleneglycol)monomethyl ether and poly(ethylene glycol) (PEG), silica gel, cellulose, acrylic acid grafted polypropylene, and the like. Additionally, the solid support contains a reactive moiety suitable for attaching the linking group component. Suitably reactive moieties include, for example, a carboxylic acid, alcohol, amine, halomethyl and the like which is used to covalently attach the linking group component during construction of the present support-bound activators. Many of these supports are available as functional polymers having reactive groups. Examples of such supports, include, by way of example, Acryloyl Wang resin, REM resin, Vinyl polystyrene, Vinylsulfonylmethyl polystyrene, (3-Formylindolyl)acetamidomethyl polystyrene, 2-(3,5-

Dimethoxy-4-formylphenoxy)ethoxymethyl polystyrene, 2-(4-Formyl-3-methoxyphenoxy)ethyl polystyrene, 4-(4-Formyl-3-methoxyphenoxy)butyryl AM resin, 4-Benzyloxybenzaldehyde polystyrene, Aldehyde Wang resin, Formylpolystyrene, 1% DVB, NovaSyn® TG acetal resin, Polystyrene-CHO, Carboxypolystyrene, NovaSyn® TG carboxy resin, Polystyrene-COOH, 4-(2',4'-Dimethoxyphenyl-Fmoc-aminomethyl)-phenoxy resin, 4-Methylbenzhydrylamine resin HCl, 4-Methylbenzhydrylamine resin HCl, 9-Fmoc-amino-xanthen-3-yloxy, 9-Fmoc-amino-xanthen-3-yloxy, Amino-(4-methoxyphenyl)methyl polystyrene, Ethylamino-xanthen-3-yloxy-Merrifield resin, NovaSyn® TG Sieber resin, NovaSyn® TGR resin, Rink Amide AM resin, Rink Amide MBHA resin, Rink amide NovaGel™, Rink amide PEGA resin, Rink Amide resin, Sieber Amide resin, Sieber Ethylamide resin, Amino methyl resin, Amino PEGA resin, Aminomethyl NovaGel™, Aminomethylated polystyrene, N-Methylaminomethyl polystyrene, 4-Fmoc-hydrazinobenzoyl AM resin, 1H-Benzotriazole polystyrene, Benzotriazole-5-carbamidomethyl polystyrene, N-Fmoc-N-methoxy-β-alanine AM resin, Weinreb AM resin, 4-Sulfamylbenzoyl AM resin, (±)-1-(2,3-Isopropylidene) glycerol polystyrene, (±)-2,2-Dimethyldioxolan-4-methoxymethyl polystyrene, (±)-1-Glycerol polystyrene, 4-(2',4'-Dimethoxyphenyl-hydroxymethyl)-phenoxy resin, 4-(2',4'-Dimethoxyphenyl-hydroxymethyl)-phenoxy resin, 4-(2',4'-Dimethoxyphenyl-hydroxymethyl)-phenoxy resin, 4-Hydroxymethyl-3-methoxyphenoxybutyric acid AM resin, 4-Hydroxymethyl-3-methoxyphenoxybutyric acid BHA resin, 4-Hydroxymethyl-3-methoxyphenoxybutyric acid MBHA resin, 4-Hydroxymethylphenoxyacetyl NovaGel™, 4-Hydroxymethylphenoxyacetyl PEGA resin, HMP resin, HMPA-NovaGel™, HMPB-AM resin, HMPB-BHA resin, HMPB-MBHA resin, Hydroxy-(2-chlorophenyl)methyl polystyrene, Hydroxymethylpolystyrene, NovaSyn® TG HMP resin, p-Benzyloxybenzyl Alcohol resin, Polystyrene-CH$_2$OH, Rink Acid resin, Trichloroacetimidate Wang resin, Wang resin, 4-Hydroxymethylbenzoic acid AM resin, 4-Hydroxymethylbenzoic acid NovaGel™, 4-Hydroxymethylbenzoic acid PEGA resin, 4-Hydroxyphenylsulfanylmethyl polystyrene, 9-(Hydroxymethyl)fluorene-4-carboxamidomethyl polystyrene, HESM polystyrene, HMBA-AM resin, HMBA-NovaGel™, HMBA-PEGA resin, Hydroxyethylsulfanylmethyl polystyrene, NovaSyn® TG HMBA resin, NovaSyn® TG hydroxy resin, Oxime resin, Aminoethyl photolinker resin, Hydroxyethyl photolinker resins, Hydroxymethyl photolinker resins, 3-[4-(Tritylmercapto)phenyl]propionyl AM resin, Mercaptomethyl polystyrene, NovaSyn® TG tritylthiol resin, Thiol 2-chlorotrityl resin, Thiol 4-methoxytrityl resin, (4-Bromophenyl)diisopropylsilyloxymethyl polystyrene, (4-Formylphenyl)diisopropylsilyloxymethyl polystyrene, 4-Trityloxyphenyl)diisopropylsilyloxymethyl polystyrene. Solid supports also include TENTAGEL™, HYPOGEL™, JANDAJEL™, AND ARGOGEL™. Other solid supports include PEGylated polystyrene (polystyrene derivatized with polyethylene glycol), Tentagel-NH$_2$ resin, and derivatized Tentagel-NH$_2$ resin (e.g., by treatment with acetyl chloride followed by reduction with LiAlH$_4$ to provide Tentagel-NHEt resin). See also the Novabiochem Catalogue 2000 for additional resins and immobilized functional groups.

Such supports may take any size, shape or form, including particulate and non-particulate forms or shapes, spheres, disks, pellets, sheets, plugs, pins, crowns, lanterns, in beaded and non-beaded forms, resins, gels, microspheres, as well as amorphous forms and shapes. Embodiments of particulate supports, include beads, pellets, disks, amorphous particles, or other conventional forms. The solid or semi-solid supports may be used as single particle, as groups of particles, as free flowing particles, and may be packed into columns, tubes or other flow-through devices. In a one embodiment, the diameter of the particulate support is 20-2000 micron, preferably 75-500 micron, more preferably 100-200 micron. As one skilled in the art will readily recognize, the scope of the present invention is not limited to the size, form, or shape of the solid or semi-solid support.

The linking group component can have a variety of structures. The liking group component is one which provides suitable spacing for the target group to interact freely with molecules or reactive components exposed to the target group. The liking group component is preferably 6-50 atoms long, more preferably 8-40 atoms long, even more preferably 8-30 atoms long, and yet more preferably 8-20 atoms long, thus providing sufficient exposure for the attached target group. Additionally, the linking group component, prior to attachment to the support, will have a attaching portion and a longer chain portion. The attaching portion is that part of the linking group component which can be directly attached to the solid support. This portion can be attached to the solid support via carbon-carbon bonds using, for example, supports having exposed (poly)trifluorochloroethylene moieties, or preferably, by siloxane bonds (using, for example, glass or silicon oxide as the solid support). Siloxane bonds the support are formed in one embodiment via reactions of attaching portions bearing trichlorosilyl or trialkoxysilyl groups. The attaching groups will also have a site for attachment of the longer chain portion. For example, groups which are suitable for attachment to a longer chain portion would include amines, hydroxyl, thiol, and carboxyl.

One skilled in the art will recognize that many additional methods of attaching linkers to solid and semi-solid supports exist. One method uses an amino resin to which an acid-bearing linker is attached via conventional techniques. Another method is the use of aryl ether linkages by coupling a phenol to a Merrifield (or equivalent) resin.

The longer chain portion of the linking group can be any of a variety of molecules which are inert to the subsequent conditions described in further detail below. These longer chain portions can be ethylene glycol oligomers containing 2-14 monomer units, or more preferably 2-10 monomer units, and even more preferably 2-8 monomer units; in addition, the longer chain portions can be diamines, diacids, amino acids, peptides, or combinations thereof. In some embodiments, the longer chain portion also comprises an activator enhancing portion, i.e., a portion that increases the reactivity of the target group relative to an alkylene or ethylene glycol linking group. More particularly, an activator enhancing portion is one that provides additional electron withdrawing character to the target group.

In another group of embodiments, L comprises an activator enhancing portion selected from the group consisting of:

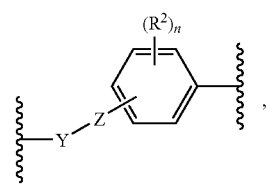

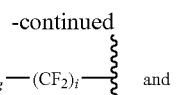

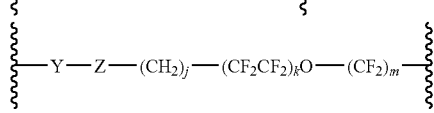

wherein Y is a member selected from the group consisting of a chemical bond, O, CO, S, and $NR^1$; Z is a member selected from the group consisting of a chemical bond or CO; each $R^2$ is independently a member selected from the group consisting of hydrogen, halogen, $(C_1-C_8)$alkyl, $(C_1-C_8)$alkoxy, $(C_2-C_8)$heteroalkyl, $(C_1-C_8)$alkylthio, $(C_1-C_8)$alkylamino, di$(C_1-C_8)$alkylamino, cyano, nitro and $(C_1-C_8)$alkylsulfonyl; the subscript 'g' is an integer selected from the group consisting of 0, 1, 2, 3, 4, 5, 6, 7, 8, 9, and 10; the subscript 'i' is an integer selected from the group consisting of 1, 2, 3, 4, 5, and 6; the subscript 'j' is an integer selected from the group consisting of 0, 1, 2, 3, 4, 5, 6, 7, 8, 9, and 10; the subscript 'k' is an integer selected from the group consisting of 1, 2, 3, and 4; the subscript 'm' is an integer selected from the group consisting of 2 and 3; and the subscript 'n' is an integer selected from the group consisting of 0, 1, 2, 3, and 4. In the groups described herein as dialkylamino, the alkyl groups can be the same or different, or can optionally be combined to form a ring having additional heteroatoms (e.g., pyrrolidino, morpholino, piperazino).

In still other embodiments, each solid or semi-solid support comprises a plurality of target groups, with a density of at least 1 nmol target groups per gram of solid or semi-solid support, more preferably, at least 1 μmol target groups per gram of solid or semi-solid support, and even more preferably, at least 1 mmol target groups per gram of solid or semi-solid support.

In other embodiments, the support-activated target can be cleaved from the solid or semi-solid support by a reagent. In one group of embodiments, the reagent comprises a nucleophile; the cleavage step may also be promoted by a transition metal catalyst. Once cleaved from the support, the resulting compound can be isolated and characterized by methods standard to the synthesis of organic compounds. As one skilled in the art will readily recognize, the present invention is not limited by the particular use of the resulting compound.

Libraries of Support-Activated Targets

In another aspect, the present invention provides a library of support-activated targets comprising a plurality of support-activated target members, wherein each support-activated target member further comprises a solid or semi-solid support; an activating group covalently attached to the solid or semi-solid support, wherein the activating group has the formula:

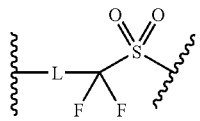

wherein L is an linking group component; and a target group covalently attached to the activating group; wherein the target group of at least one support-activated target member in the library is different from the target group of at least one other support-activated target member in the library.

The description of the support-activated targets presented above is incorporated into this aspect of the present invention. As one skilled in the art will readily recognize, the present invention is not limited by the number of different support-activated target members in the library. Each support-activated target member of the library can be cleaved from its solid or semi-solid support by a reagent. In one set of embodiments the reagent comprises a nucleophile; the cleavage step may also be promoted by a transition metal catalyst. The support-activated targets and the resulting compounds can be used for a variety of purposes, including assays, screens, analysis, and testing. As one skilled in the art will readily recognize, the present invention is not limited by the particular use of the resulting compounds.

Linker Reagents

In view of the above, the present invention further provides linker reagents having the formula:

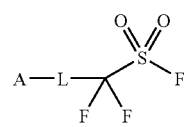

(II)

wherein L is a liking group component; and A is an attaching group.

In one embodiment, the attaching group is a member selected from the group consisting of $NH_2$, NHR, $CO_2H$, $CO_2R$, C(O)Cl, OH, SH, and protected forms thereof, wherein each R is a member independently selected from the group consisting of substituted $(C_1-C_8)$alkyl, unsubstituted $(C_1-C_8)$alkyl, substituted aryl, and unsubstituted aryl. In one embodiment, A is $NH_2$ or $CH_2$-halogen.

In further embodiments, L is selected from:

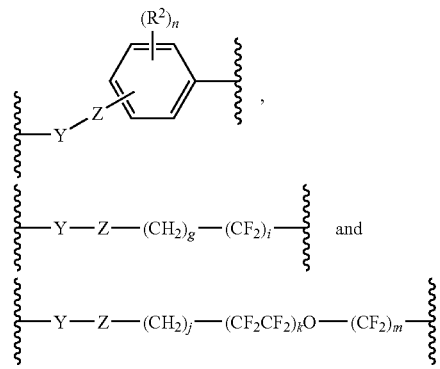

wherein Y is a member selected from the group consisting of a chemical bond, O, CO, S, $NR^1$; Z is a member selected from the group consisting of a chemical bond or CO; each $R^2$ is independently a member selected from the group consisting of hydrogen, halogen, $(C_1-C_8)$alkyl, $(C_1-C_8)$alkoxy, $(C_2-C_8)$ heteroalkyl, $(C_1-C_8)$alkylthio, $(C_1-C_8)$alkylamino, di$(C_1-C_8)$ alkylamino, cyano, nitro and $(C_1-C_8)$alkylsulfonyl; the subscript 'g' is an integer selected from the group consisting of 0, 1, 2, 3, 4, 5, 6, 7, 8, 9, and 10; the subscript 'i' is an integer selected from the group consisting of 1, 2, 3, 4, 5, and 6; the subscript 'j' is an integer selected from the group consisting of 0, 1, 2, 3, 4, 5, 6, 7, 8, 9, and 10; the subscript 'k' is an integer selected from the group consisting of 1, 2, 3, and 4; the subscript 'm' is an integer selected from the group consisting of 2 and 3; and the subscript 'n' is an integer selected from the group consisting of 0, 1, 2, 3, and 4. In the groups described herein as dialkylamino, the alkyl groups can be the same or different, or can optionally be combined to form a ring having additional heteroatoms (e.g., pyrrolidino, morpholino, piperazino).

In one group of embodiments, the linker reagent has the formula:

HO$_2$C—(CH$_2$)$_j$—(CF$_2$CF$_2$)$_k$O—(CF$_2$)$_2$—SO$_2$F wherein the subscript j is an integer selected from the group consisting of 0, 1, 2, 3, 4, 5, 6, 7, 8, 9, and 10; and the subscript k is an integer selected from the group consisting of 1, 2, 3, 4, 5, 6, 7, and 8. In one particular embodiment, the subscript j is 1 and the subscript k is 1.

In other embodiments, the linker reagent has the formula:

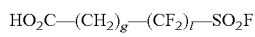
HO$_2$C—(CH$_2$)$_g$—(CF$_2$)$_i$—SO$_2$F wherein the subscript g is an integer selected from the group consisting of 3, 4, 5, and 6; and the subscript i is an integer selected from the group consisting of 0, 1, 2, 3, 4, 5, 6, 7, 8, 9 and 10.

In other embodiments, the linker reagent has the formula:

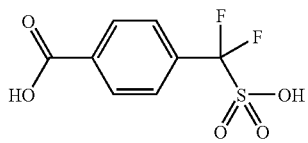

Other embodiments are those represented by formulae C and D:

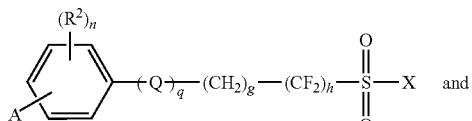

C

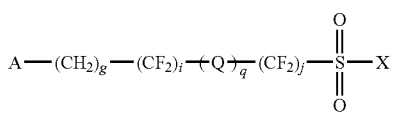

D in which X is F, Cl, trisubstituted silyloxy or OH; Q is O; A is C(O)Cl, CO$_2$H or OH; and each R$^2$ is as defined above. The subscripts for formulae C and D are as follows: the subscript 'g' is an integer selected from the group consisting of 0, 1, 2, 3, 4, 5, 6, 7, 8, 9, 10, and 11; the subscript 'h' is an integer selected from the group consisting of 1, 2, 3, 4, 5, 6, 7, and 8; the subscript 'i' is an integer selected from the group consisting of 0, 1, 2, 3, 4, 5, 6, 7, and 8; the subscript 'j' is an integer selected from the group consisting of 1, 2, 3, and 4; the subscript 'n' is an integer selected from the group consisting of 0, 1, 2, 3, and 4; and the subscript 'q' is an integer selected from the group consisting of 0, and 1. In one embodiment, X is F; Q is O; A is COOH and each R$^2$ is H.

Preparation of Linker Reagents and Support-Bound Activators

The polymer-supported perfluorosulfonyl fluoride linker of the present invention can be prepared as outlined in FIG. 1.

FIG. 1

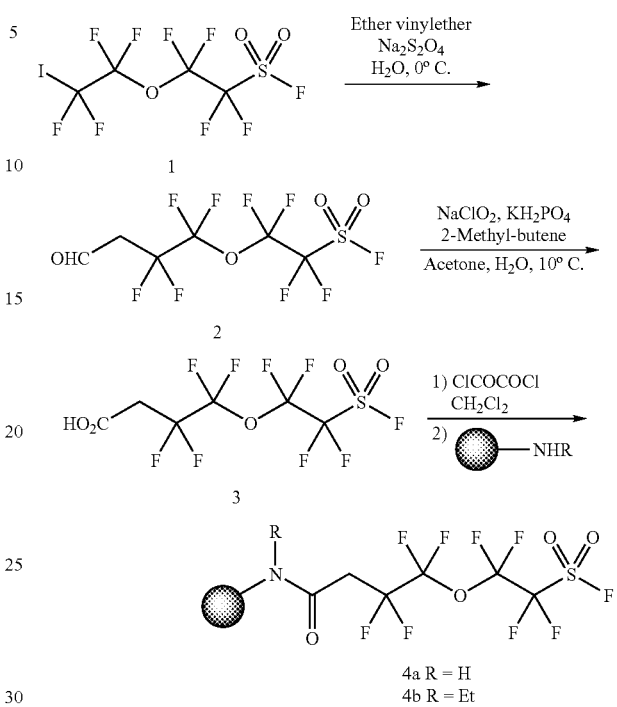

4a R = H
4b R = Et

FIG. 1 illustrates the preparation of a linker FIG. 1, Structure 3 and a support-bound activator FIG. 1, Structure 4 from commercially available sulfonyl fluoride FIG. 1, Structure 1 (Aldrich Chemical Co., Milwaukee, Wis., U.S.A.). Thus, treatment of iodide FIG. 1, Structure 1 with ethyl vinyl ether in the presence of sodium thiosulfate provides the aldehyde FIG. 1, Structure 2. Oxidation of the aldehyde provides the carboxylic acid FIG. 1, Structure 3 which is suitable for attaching to a solid or semi-solid support via an amide- or ester-forming reaction with a suitable nucleophile on the support (e.g., an amino or hydroxy group). Alternatively, the carboxylic acid FIG. 1, Structure 3, can be converted to its acid chloride using, for example, oxalyl chloride and then reacted with a suitable amine resin (e.g., Tentagel-NH$_2$ or Tentagel-NHEt). In still other embodiments, the aldehyde FIG. 1, Structure 2 can be attached to a resin via a reductive amination reaction of an amine resin, aldehyde FIG. 1, Structure 2 and a suitable reducing agent such as sodium borohydride.

Figure 2:
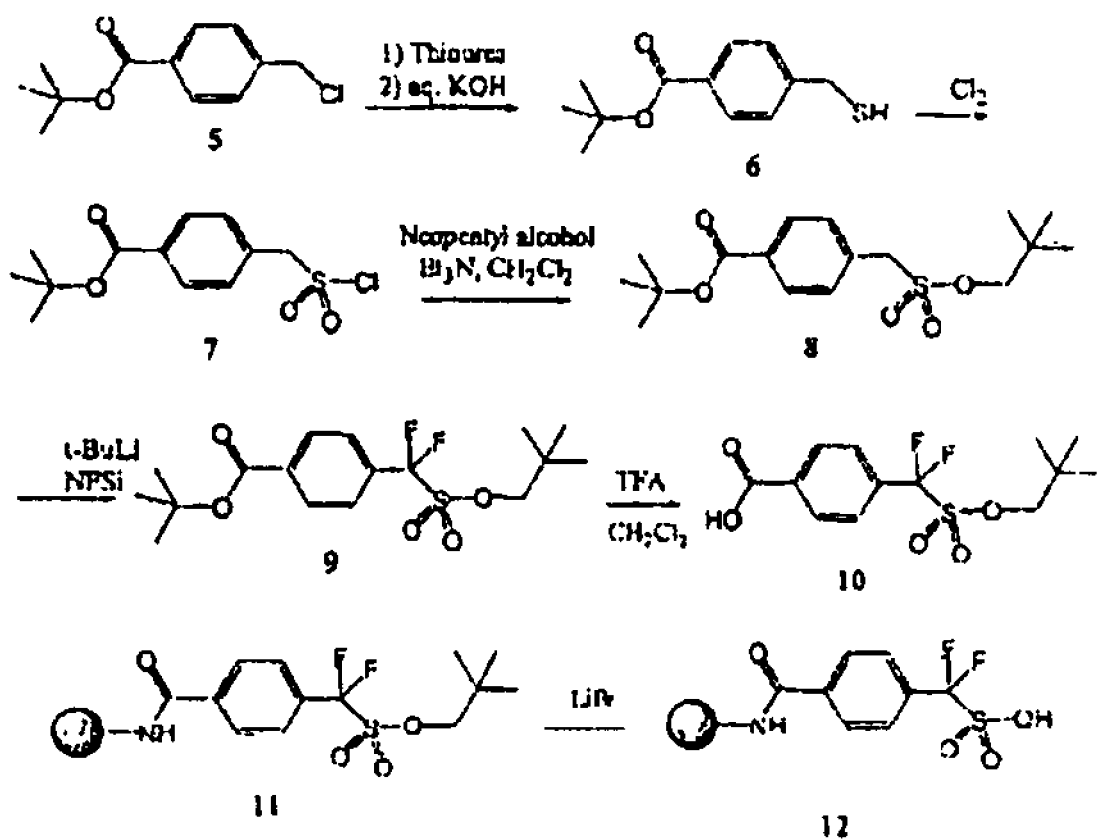
FIG. 2 illustrates a synthetic scheme for the preparation of a support-bound perfluorosulfonic acid in accordance with the present invention.

FIG. 2 illustrates the preparation of another linker reagent starting with 4-chloromethyl benzoyl chloride (Aldrich Chemical Co., Milwaukee, Wis., U.S.A.).

FIG. 2

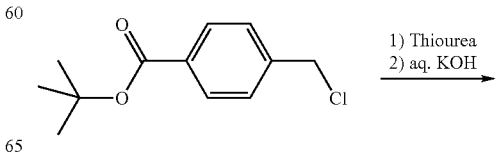

5

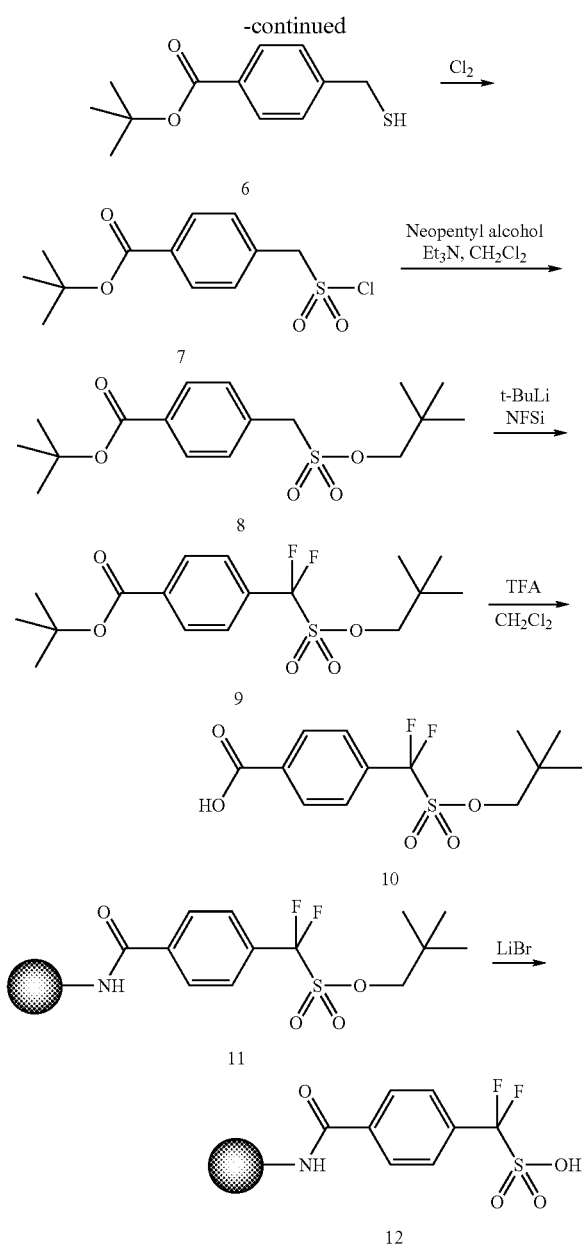

Thus, treatment of 4-chloromethyl benzoyl chloride with t-butanol and triethylamine provides the ester FIG. 2, Structure 5 which can be converted to the thiol FIG. 2, Structure 6 upon treatment with thiourea, followed by hydrolysis with aqueous KOH. Oxidation of the thiol FIG. 2, Structure 6 with chlorine provides the sulfonyl chloride FIG. 2, Structure 7. Conversion of the sulfonyl chloride to the sulfonate ester FIG. 2, Structure 8 can be accomplished with neopentyl alcohol in the presence of base (e.g., Et₃N). The sulfonate ester can then be activated by the stepwise exchange of the a hydrogen atoms with fluorine atoms (tBuLi and NFSi) to give the ester FIG. 2, Structure 9. Deprotection of the carboxylic ester with 20% TFA in methylene chloride provides the linker reagent FIG. 2, Structure 10. The remaining steps in FIG. 2 illustrate the attachment of the linker reagent to a support and the conversion to a sulfonic acid FIG. 2, Structure 12.

Methods of Using the Support-Bound Activators

In yet another aspect, the present invention provides a method for covalently attaching a nucleophile to a compound having a hydroxy group or an enolizable ketone, the method comprising, (a) contacting a compound having a hydroxy group or an enolizable ketone with a support-bound activator, wherein said contacting a compound having a hydroxy group or an enolizable ketone with a support bound activator forms an activated complex; and (b) contacting the activated complex with a reagent comprising a nucleophile under conditions sufficient to covalently attach the nucleophile to the compound.

In one embodiment, the support-bound activator has the formula:

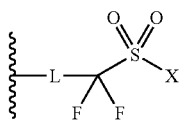

wherein L is a linking group component; X is a member selected from the group consisting of F, and Cl; wherein the support-bound activator is covalently attached to a solid or semi-solid support.

Turning first to the solid or semi-solid support, the present invention is useful in a variety of solid-phase synthesis applications and, accordingly, a variety of supports find utility in this aspect of the invention. Typical solid supports include, but are not limited to, cross-linked divinylbenzene-styrene (polystyrene), controlled pore glass (CPG), polyacrylamides, poly(ethyleneglycol)monomethyl ether and poly(ethylene glycol) (PEG), silica gel, cellulose, acrylic acid grafted polypropylene, and the like. Additionally, the solid support contains a reactive moiety suitable for attaching the linking group component. Suitably reactive moieties include, for example, a carboxylic acid, alcohol, amine, halomethyl and the like which is used to covalently attach the linking group component during construction of the present support-bound activators. Many of these supports are available as functional polymers having reactive groups. Examples of such supports, include, by way of example, Acryloyl Wang resin, REM resin, Vinyl polystyrene, Vinylsulfonylmethyl polystyrene, (3-Formylindolyl)acetamidomethyl polystyrene, 2-(3,5-Dimethoxy-4-formylphenoxy)ethoxymethyl polystyrene, 2-(4-Formyl-3-methoxyphenoxy)ethyl polystyrene, 4-(4-Formyl-3-methoxyphenoxy)butyryl AM resin, 4-Benzyloxybenzaldehyde polystyrene, Aldehyde Wang resin, Formylpolystyrene, 1% DVB, NovaSyn® TG acetal resin, Polystyrene-CHO, Carboxypolystyrene, NovaSyn® TG carboxy resin, Polystyrene-COOH, 4-(2',4'-Dimethoxyphenyl-Fmoc-aminomethyl)-phenoxy resin, 4-Methylbenzhydrylamine resin HCl, 4-Methylbenzhydrylamine resin HCl, 9-Fmoc-amino-xanthen-3-yloxy, 9-Fmoc-amino-xanthen-3-yloxy, Amino-(4-methoxyphenyl)methyl polystyrene, Ethylamino-xanthen-3-yloxy-Merrifield resin, NovaSyn® TG Sieber resin, NovaSyn® TGR resin, Rink Amide AM resin, Rink Amide MBHA resin, Rink amide NovaGel™, Rink amide PEGA resin, Rink Amide resin, Sieber Amide resin, Sieber Ethylamide resin, Amino methyl resin, Amino PEGA resin, Aminomethyl NovaGel™, Aminomethylated polystyrene, N-Methylaminomethyl polystyrene, 4-Fmoc-hydrazinobenzoyl AM resin, 1H-Benzotriazole polystyrene, Benzotriazole-5-carbamidomethyl polystyrene, N-Fmoc-N-methoxy-β-alanine AM resin, Weinreb AM resin, 4-Sulfamylbenzoyl AM resin, (±)-1-(2,3-Isopropylidene) glycerol polystyrene, (±)-2,2-Dimethyldioxolan-4-methoxymethyl polystyrene, (±)-1-Glycerol polystyrene, 4-(2',4'-Dimethoxyphenyl-hydroxymethyl)-phenoxy resin, 4-(2',4'-Dimethoxyphenyl-hydroxymethyl)-phenoxy resin, 4-(2',4'-Dimethoxyphenylhydroxymethyl)-phenoxy resin, 4-Hydroxymethyl-3-methoxyphenoxybutyric acid AM resin, 4-Hydroxymethyl-3-methoxyphenoxybutyric acid BHA resin, 4-Hydroxymethyl-3-methoxyphenoxybutyric acid MBHA resin, 4-Hydroxymethylphenoxyacetyl NovaGel™, 4-Hydroxymethylphenoxyacetyl PEGA resin, HMP resin, HMPA-NovaGel™, HMPB-AM resin, HMPB-BHA resin, HMPB-MBHA resin, Hydroxy-(2-chlorophenyl)methyl polystyrene, Hydroxymethylpolystyrene, NovaSyn® TG HMP resin, p-Benzyloxybenzyl Alcohol resin, Polystyrene-CH$_2$OH, Rink Acid resin, Trichloroacetimidate Wang resin, Wang resin, 4-Hydroxymethylbenzoic acid AM resin, 4-Hydroxymethylbenzoic acid NovaGel™, 4-Hydroxymethyl-benzoic acid PEGA resin, 4-Hydroxyphenylsulfanylmethyl polystyrene, 9-(Hydroxymethyl)fluorene-4-carboxamidomethyl polystyrene, HESM polystyrene, HMBA-AM resin, HMBA-NovaGel™, HMBA-PEGA resin, Hydroxyethylsulfanylmethyl polystyrene, NovaSyn® TG HMBA resin, NovaSyn® TG hydroxy resin, Oxime resin, Aminoethyl photolinker resin, Hydroxyethyl photolinker resins, Hydroxymethyl photolinker resins, 3-[4-(Tritylmercapto)phenyl]propionyl AM resin, Mercaptomethyl polystyrene, NovaSyn® TG tritylthiol resin, Thiol 2-chlorotrityl resin, Thiol 4-methoxytrityl resin, (4-Bromophenyl)diisopropylsilyloxymethyl polystyrene, (4-Formylphenyl)diisopropylsilyloxymethyl polystyrene, (4-Trityloxyphenyl)diisopropylsilyloxymethyl polystyrene. Solid supports also include TENTAGEL™, HYPOGEL™, JANDAJEL™, AND ARGOGEL™. Other solid supports include PEGylated polystyrene (polystyrene derivatized with polyethylene glycol), Tentagel-NH$_2$ resin, and derivatized Tentagel-NH$_2$ resin (e.g., by treatment with acetyl chloride followed by reduction with LiAlH$_4$ to provide Tentagel-NHEt resin). See also the Novabiochem Catalogue 2000 for additional resins and immobilized functional groups.

Such supports may take any size, shape or form, including particulate and non-particulate forms or shapes, spheres, disks, pellets, sheets, plugs, pins, crowns, lanterns, in beaded and non-beaded forms, resins, gels, microspheres, as well as amorphous forms and shapes. Embodiments of particulate supports, include beads, pellets, disks, amorphous particles, or other conventional forms. The solid or semi-solid supports may be used as single particle, as groups of particles, as free flowing particles, and may be packed into columns, tubes or other flow-through devices. In a one embodiment, the diameter of the particulate support is 20-2000 micron, preferably 75-500 micron, more preferably 100-200 micron. As one skilled in the art will readily recognize, the scope of the present invention is not limited to the size, form, or shape of the solid or semi-solid support.

The linking group component can have a variety of structures. The linking group component is one which provides suitable spacing for the activator portion (—CF$_2$—SO$_2$—X) to interact freely with molecules or reactive components exposed to the activator portion. The linking group component is preferably 6-50 atoms long, more preferably 8-40 atoms long, even more preferably 8-30 atoms long, and yet more preferably 8-20 atoms long, thus providing sufficient exposure for the attached activator portion. Additionally, the linking group component, prior to attachment to the support, will have a attaching portion and a longer chain portion. The attaching portion is that part of the linking group component which can be directly attached to the solid support. This portion can be attached to the solid support via carbon-carbon bonds using, for example, supports having exposed (poly) trifluorochloroethylene moieties, or preferably, by siloxane bonds (using, for example, glass or silicon oxide as the solid support). Siloxane bonds the support are formed in one embodiment via reactions of attaching portions bearing trichlorsilyl or trialkoxysilyl groups. The attaching groups will also have a site for attachment of the longer chain portion. For example, groups which are suitable for attachment to a longer chain portion would include amines, hydroxyl, thiol, and carboxyl.

One skilled in the art will recognize that many additional methods of attaching linkers to solid and semi-solid supports exist. One method uses an amino resin to which an acid-bearing linker is attached via conventional techniques. Another method is the use of aryl ether linkages by coupling a phenol to a Merrifield (or equivalent) resin.

The longer chain portion can be any of a variety of molecules which are inert to the subsequent conditions used in the activator reactions described in further detail below. These longer chain portions can be ethylene glycol oligomers containing 2-14 monomer units, or more preferably 2-10 monomer units, and even more preferably 2-8 monomer units; in addition, the longer chain portions can be diamines, diacids, amino acids, peptides, or combinations thereof. In some embodiments, the longer chain portion also comprises an activator enhancing portion, i.e., a portion that increases the reactivity of the activator relative to an alkylene or ethylene glycol liking group. More particularly, an activator enhancing portion is one that provides additional electron withdrawing character to the activator portion (e.g., the —CF$_2$—SO$_2$—X portion).

In one group of embodiments, X is a member selected from the group consisting of F and Cl. In another group of embodiments, L comprises an activator enhancing portion selected from the group consisting of:

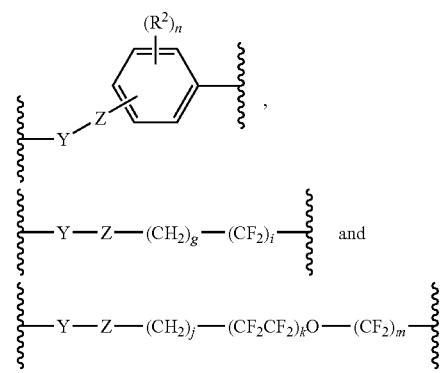

wherein Y is a member selected from the group consisting of a chemical bond, O, CO, S, and NR$^1$; Z is a member selected from the group consisting of a chemical bond or CO; each R$^2$ is independently a member selected from the group consisting of hydrogen, halogen, (C$_1$-C$_8$)alkyl, (C$_1$-C$_8$)alkoxy, (C$_2$-C$_8$)heteroalkyl, (C$_1$-C$_8$)alkylthio, (C$_1$-C$_8$)alkylamino, di(C$_1$-C$_8$)alkylamino, cyano, nitro and (C$_1$-C$_8$)alkylsulfonyl; the subscript 'g' is an integer selected from the group consisting of 0, 1, 2, 3, 4, 5, 6, 7, 8, 9, and 10; the subscript 'i' is an integer selected from the group consisting of 1, 2, 3, 4, 5, and 6; the subscript 'j' is an integer selected from the group consisting of 0, 1, 2, 3, 4, 5, 6, 7, 8, 9, and 10; the subscript 'k' is an integer selected from the group consisting of 1, 2, 3, and 4; the subscript 'm' is an integer selected from the group consisting of 2 and 3; and the subscript 'n' is an integer selected from the group consisting of 0, 1, 2, 3, and 4. In the groups described herein as dialkylamino, the alkyl groups can be the same or different, or can optionally be combined to form a ring having additional heteroatoms (e.g., pyrrolidino, morpholino, piperazino).

In another embodiment, the support-bound activator is available in kit form for use in solid phase organic chemistry, as a reagent or catalyst in solution phase organic chemistry, as a scavenger resin in solution phase organic chemistry, as a silylating agent for use in analytical chemistry, and in particular, in chromatography, and as a reagent for the production of PET-ready molecules.

In one group of embodiments, the support-bound activators of the present invention are:

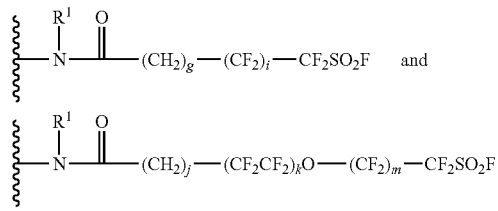

wherein the symbol $R^1$ and the subscripts g, i, j, k and m all have the meanings provided above.

In another group of embodiments, the support-bound activators have a formula selected from:

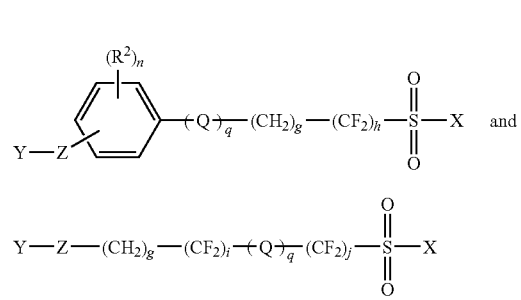

In each of formulae A and B, X can be F and Cl; Q is O; Z is a chemical bond or C=O; Y is O-support or $NR_1$-support wherein $R_1$ is H, $(C_1-C_8)$alkyl or aryl and the support is a PEG-modified polystyrene or a Merrifield resin; and each $R^2$ is as defined more generally above. The subscripts in formulae A and B are as follows: 'g' is an integer selected from the group consisting of 0, 1, 2, 3, 4, 5, 6, 7, 8, 9, 10, and 11; 'h' is an integer selected from the group consisting of 1, 2, 3, 4, 5, 6, 7, and 8; 'i' is an integer selected from the group consisting of 0, 1, 2, 3, 4, 5, 6, 7, and 8; 'j' is an integer selected from the group consisting of 1, 2, 3, and 4; 'k' is an integer selected from the group consisting of 1, 2, 3, and 4; 'm' is an integer selected from the group consisting of 2 and 3; 'n' is an integer selected from the group consisting of 0, 1, 2, 3, and 4; and 'q' is an integer selected from the group consisting of 1, and 2.

In one particular embodiment in formulae A and B, X is F; Q is O; Z is C=O, Y is NH-support wherein the support is a PEG-modified polystyrene; and each $R^2$ is H.

In one group of embodiments, the reagent is a member selected from the group consisting of an organostannane compound, an organozinc compound, an organoboron compound, an organolithium compound, an organoaluminum compound, a Grignard reagent, an organosilicon compound, an organocopper compound, a thiol, a dialkylphosphite, an amine, a metal halide, and a halogen.

In one group of embodiments, the nucleophile is a member selected from the group consisting of an amine, a halogen anion, an aryl moiety, an alkyl moiety, a cyano, and a hydride. In preferred embodiments, a transition metal catalyst is used in conjunction with the nucleophilic reagent.

In still other embodiments, the activated complex is treated under the appropriate conditions to afford a radioisotopically labeled compound without significant contamination from undesired compounds. This particular embodiment is expected to find significant utility in the field of medicinal chemistry, in which the use of imaging agents remains an important technique to non-invasively evaluate human and animal conditions. One newly emerging field is that of positron emission tomography (PET). Briefly, this involves the use of short lived radioisotopes incorporated into known or potential drug substances and evaluation of their relative distribution throughout the body. One significant drawback to existing methods is the preparation of the intended labeled compound and their use before the radioisotopes has decayed below that of useful intensity. One must prepare, purify, and use the intended labeled compound within a few hours in a PET study. Merely by way of example, U.S. Pat. No. 6,307,372, entitled "Methods for high throughput chemical screening using magnetic resonance imaging" is herein incorporated by reference in its entirety. Thus, there is a need in the art for a method for rapidly preparing and purifying PET-ready molecules. An approach that would satisfy this need would be to provide support-bound targets that can be released from the support upon reaction with radioisotopically labeled nucleophiles.

For example, treatment of a support-bound aryl perfluorosulfonate species with $^{11}C$ methyl lithium promotes a cleavage/derivatization cascade which results in the release of a $^{11}C$ methyl-substituted aryl species suitable for use in a PET experiment. Another example is incorporation of $^{18}F$ into aryl species to afford arylfluorides, commonly found in drug substances.

In one embodiment, the nucleophile is an $^{18}F$ anion. The labeled compounds resulting from the reaction of the $^{18}F$ anion with the activated complex can be used as PET-ready molecules for medical imaging purposes.

In still another embodiment, the nucleophile is a $^{11}CH_3$ anion. Examples of reagents for providing the $^{11}CH_3$ anion are $^{11}C$ methyl-lithium or $^{11}C$ methyl-cuprate. The labeled compounds resulting from the reaction of the $^{11}CH_3$ anion with the activated complex can be used as PET-ready molecules for medical imaging purposes.

In yet another embodiment, the present invention provides a method for transformation or substitution of a hydroxy group in a compound having a hydroxy group or an enolizable carbonyl group, the method comprising, (a) contacting the compound having a hydroxy group or an enolizable carbonyl group with a support-bound activator having the formula:

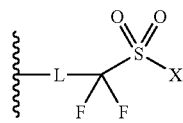

wherein L is a linking group component; X is selected from F, and Cl; and the support bound activator is covalently attached to a solid or semi-solid support, under conditions sufficient to form an activated complex having the formula:

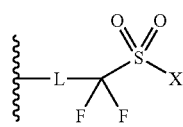

wherein —X is now —OQ and Q represents said compound; O is the oxygen atom vestige of the hydroxy group or enolizable ketone present in said compound; and L is the linking group component; and (b) contacting the activated complex with a reagent comprising a nucleophile to transform or substitute said hydroxy group and form a new compound having the formula:

R$^x$-Q.

A variety of transformations can be accomplished using the methods herein. More particularly, the transformations include deoxygenations, cross-couplings (e.g., via organometallic reagents used in Suzuki, Stille, Heck, and organozinc coupling reactions), CO insertion, cyanide displacements, and numerous other reactions known to be suitable with vinyl or aryl triflates (see, Ritter, *Synthesis* 8:735-762 (1993)).

In one group of embodiments, the hydroxy group is present on an aromatic ring system such as a substituted or unsubstituted benzene or heteroaryl ring and the reagent is a hydride source which results in the reductive cleavage of the compound Q.

Figure 3:
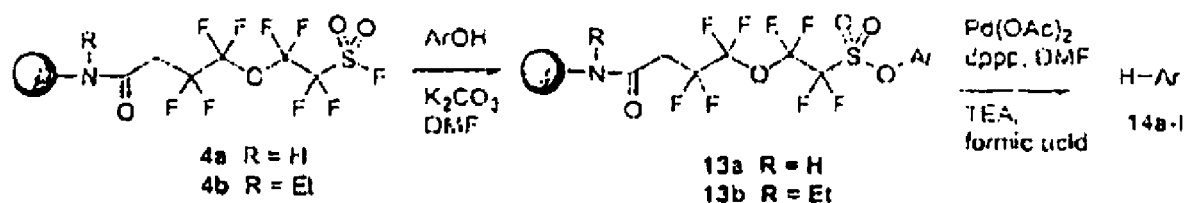
FIG. 3 illustrates a synthetic scheme for the deoxygenation reaction sequence for phenols to generate the parent arenes in accordance with the present invention.

In one particular group of embodiments, the support-bound activator is a polymer-supported perfluorosulfonate linker as shown in FIG. 3. Deoxygenation of a polymer-supported aryl perfluorosulfonate can be carried out by a palladium-mediated reduction. The polymer-bound aryl perfluorosulfonates can be efficiently cleaved with Et$_3$N/HCO$_2$H in the presence of a catalytic amount of Pd(OAc)$_2$ and 1,3-bis(diphenylphosphino)propane (dppp) in high yields to produce the reduced arenes under mild conditions. Table 1 provides examples of compounds (Q-OH) that can be reduced (Q-H) using the methods of the invention.

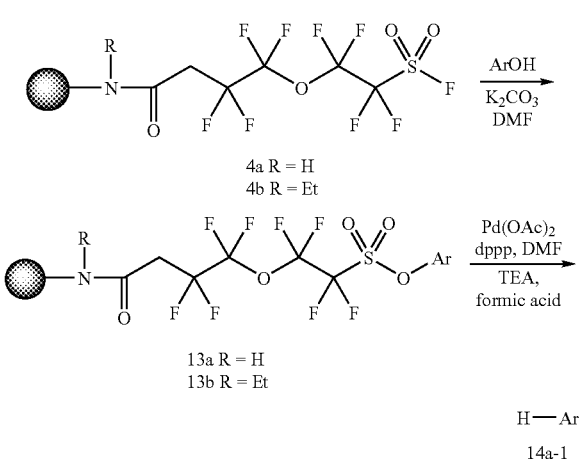

FIG. 3

TABLE 1

| | ArOH | ArH | Yield of ArH |
|---|---|---|---|
| 14a | 8-hydroxyquinoline | quinoline | 81 |
| 14b | 1-naphthol | naphthalene | 76 |
| 14c | HO-C$_6$H$_4$-NHCOCH$_3$ | C$_6$H$_5$-NHCOCH$_3$ | 88 |
| 14d | 4-hydroxybenzophenone | benzophenone | 90 |

TABLE 1-continued

| | ArOH | ArH | Yield of ArH |
|---|---|---|---|
| 14e | 2-hydroxy-1-acetylnaphthalene | 1-acetylnaphthalene | 86 |
| 14f | 4-hydroxy-3,5-dimethylacetophenone | 3,5-dimethylacetophenone | 85 |
| 14g | 4-hydroxy-3-methoxyacetophenone | 3-methoxyacetophenone | 88 |
| 14h | 4'-hydroxyflavanone | flavanone | 75 |
| 14i | 3-chloro-4-hydroxyacetophenone | 3-chloroacetophenone | 63 |
| 14j | 2-fluoro-4-hydroxyacetophenone | 2-fluoroacetophenone | 86 |
| 14k | 4-hydroxy-3-methoxybenzyl alcohol | 3-methoxybenzyl alcohol | 86 |
| 14l | bisphenol A | 4-cumylphenol | 80 |

In another particular group of embodiments, the transformation is a cross-coupling reaction. In this group of embodiments, the activated complex is

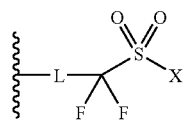

wherein —X is now —Oar and Ar is an aryl or heteroaryl group.

Figure 4:
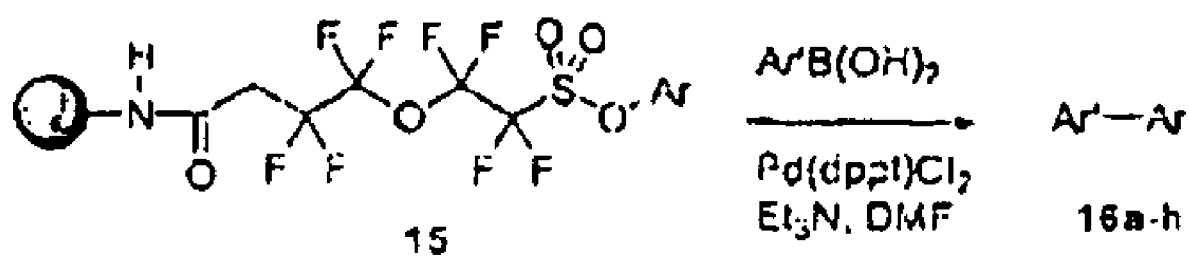
FIG. 4 illustrates a synthetic scheme to effect a cleavage/cross coupling reaction to afford biaryls in accordance with the present invention

In one group of embodiments, the reagent is an aryl boronic acid (Ar'B(OH)$_2$) which provides a coupled compound having the formula Ar—Ar'. FIG. 4 provides an illustration of this embodiment using a nonaflate linker of the present invention, and Table 2 provides an illustration of the compounds and products provided. For simplicity, the linker is not shown in Table 2.

FIG. 4

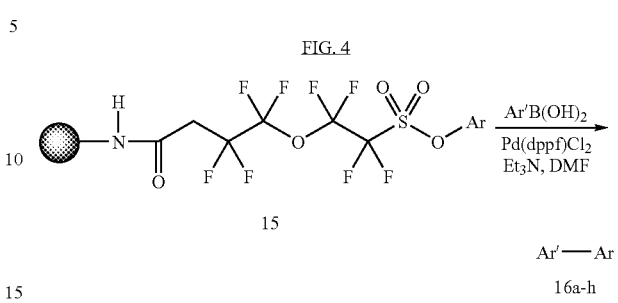

TABLE 2

| Resin | Aryl boronic acid | Product (Ar'—Ar) |
|---|---|---|
| 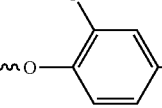 | 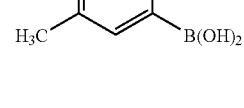 | 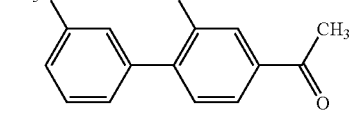 16a |
| 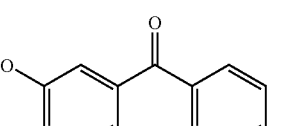 | 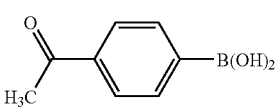 |  16b |
| 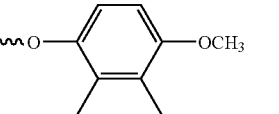 | 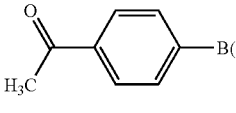 | 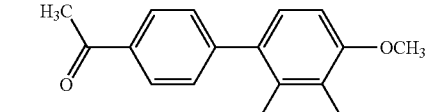 16c |
| 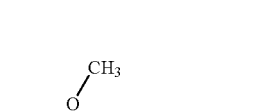 | 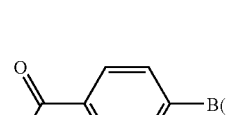 | 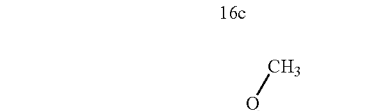 16d |
| 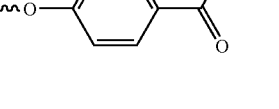 |  | 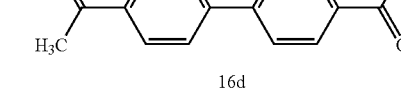 16e |

TABLE 2-continued

| Resin | Aryl boronic acid | Product (Ar'—Ar) |
|---|---|---|
| 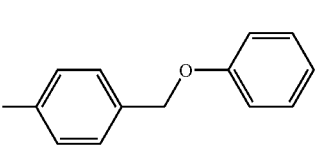 | 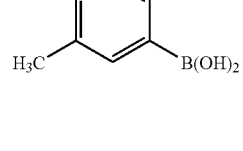 | 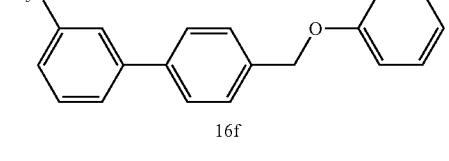<br>16f |
| 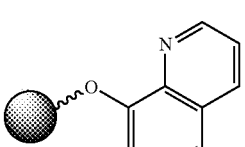 | 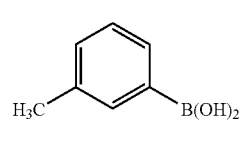 | 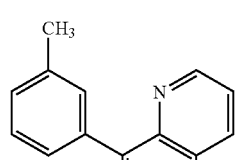<br>16g |
| 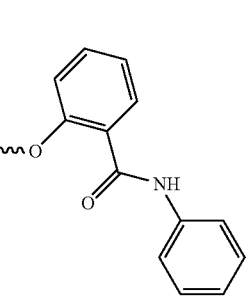 | 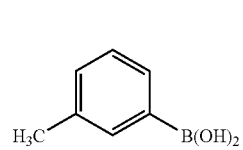 | 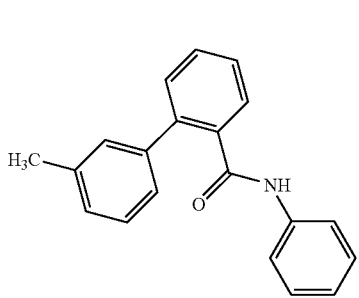<br>16h |

Figure 5:
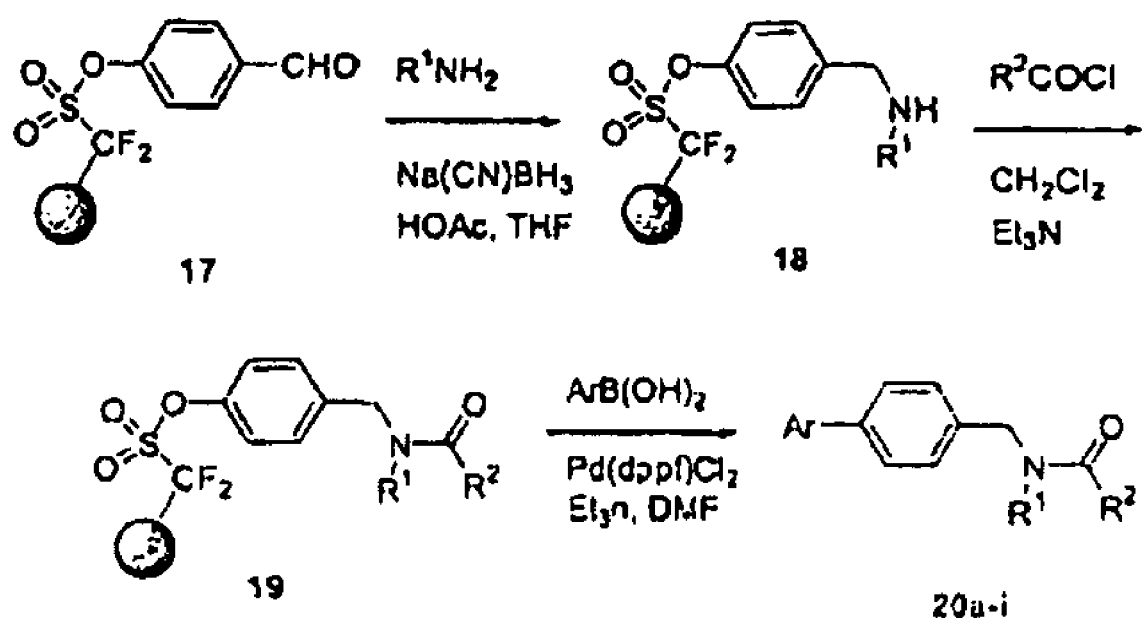
FIG. 5 illustrates a synthetic scheme whereby a library of targets are prepared on the polymer support in accordance with the present invention.

In still other embodiments, the activated complex is subjected to additional synthetic transformations prior to a cross-coupling (e.g., Suzuki, Stille, Heck, Sonogashira, Buchwald) which releases the product from the resin. FIG. 5 illustrates certain reactions that can be applied to the activated complex, while Table 3 illustrates various starting materials and products that can be obtained using the linking group/activators described herein.

FIG. 5

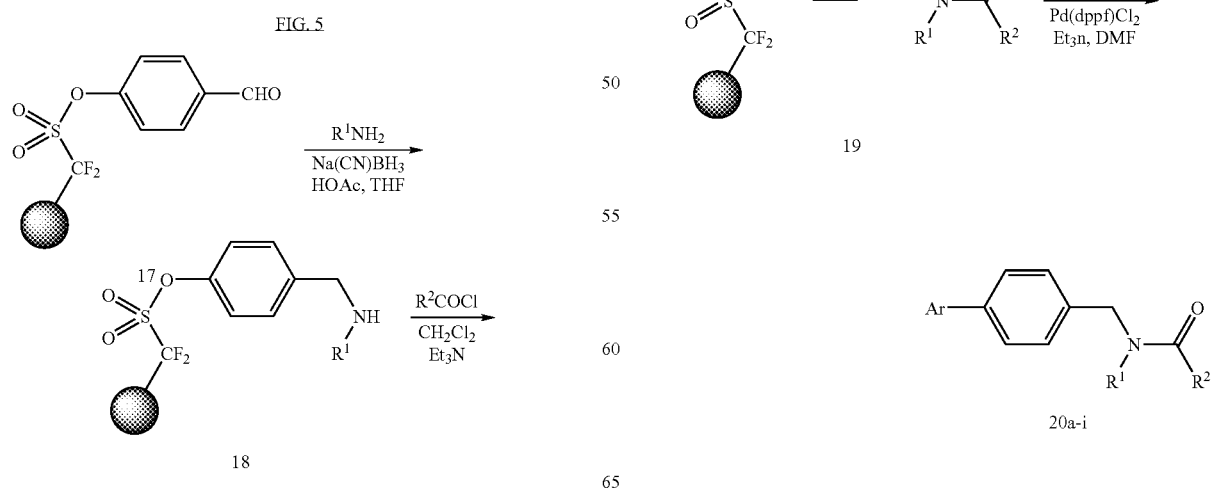

TABLE 3

| R¹NH₂ | R²COCl | Boronic Acid | Product |
|---|---|---|---|
| furfurylamine | benzoyl chloride | 3-acetylphenylboronic acid | 20a |
| furfurylamine | benzoyl chloride | 4-methoxyphenylboronic acid | 20b |
| furfurylamine | benzoyl chloride | 3-methylphenylboronic acid | 20c |
| furfurylamine | isobutyryl chloride | 4-methylphenylboronic acid | 20d |
| furfurylamine | isobutyryl chloride | 4-methoxyphenylboronic acid | 20e |

TABLE 3-continued
| R¹NH₂ | R²COCl | Boronic Acid | Product |
|---|---|---|---|
| 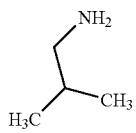 | 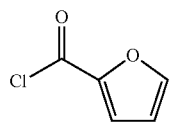 | 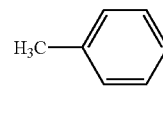 | 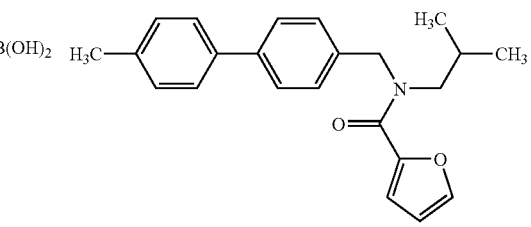<br>20f |
| 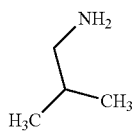 | 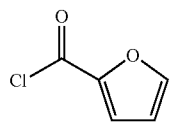 | 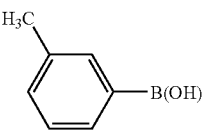 | 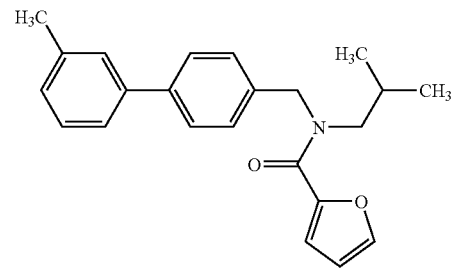<br>20g |
| 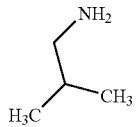 | 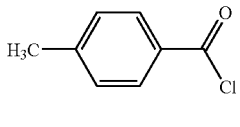 | 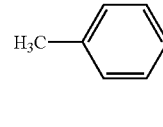 | 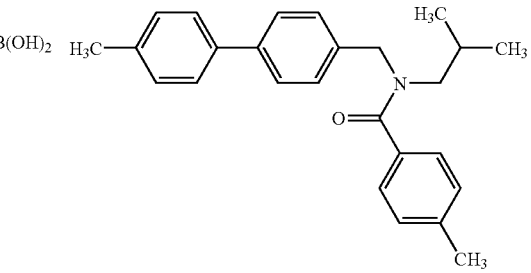<br>20h |
| 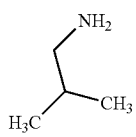 | 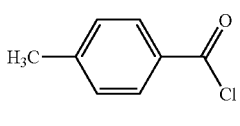 | 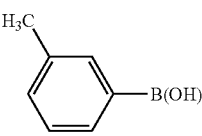 | 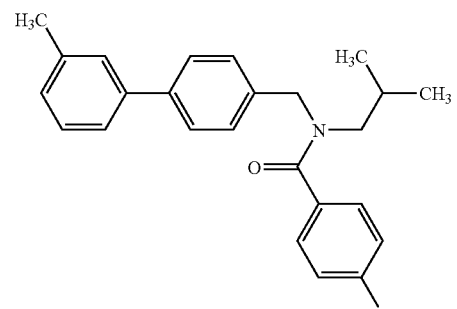<br>20i |

Figure 6:
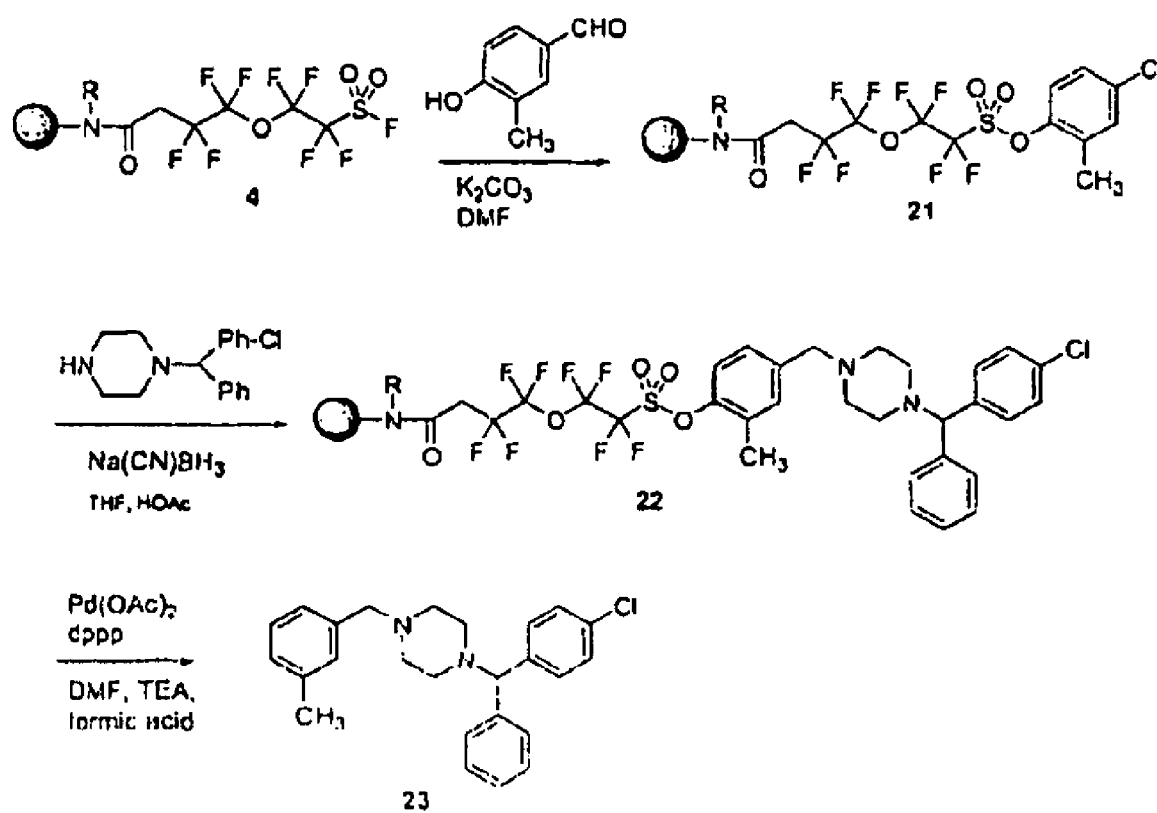
FIG. 6 illustrates the synthesis of a known drug substance and subsequent cleavage from the polymer support in accordance with the present invention.

The perfluorosulfonyl fluoride linker of this invention was used to a multi-step synthesis of the therapeutic agent, meclizine as outlined in FIG. 6.

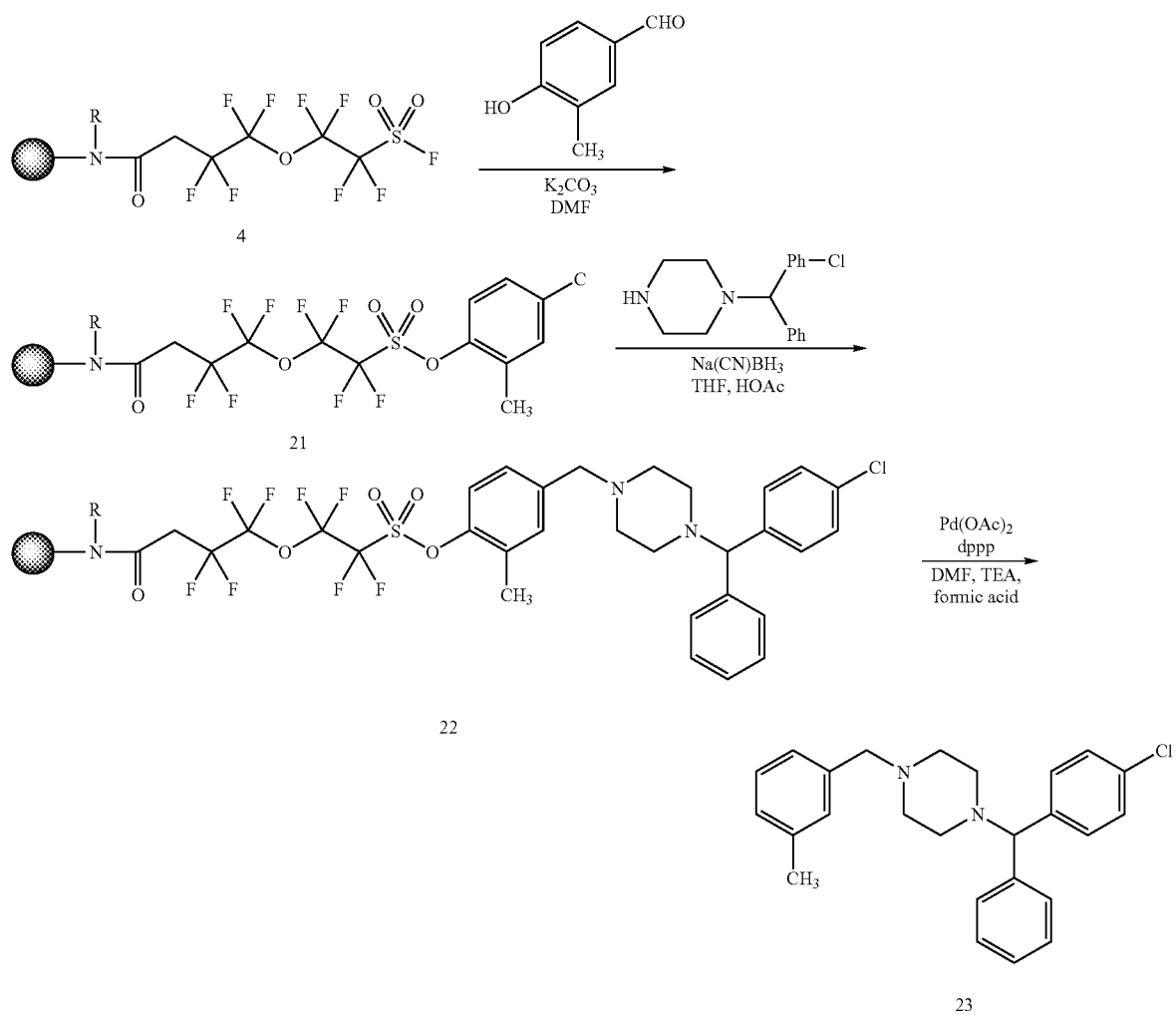

this aspect of the invention. Typical solid supports include, but are not limited to, cross-linked divinylbenzene-styrene (polystyrene), controlled pore glass (CPG), polyacrylamides, poly(ethyleneglycol)monomethyl ether and poly(ethylene glycol) (PEG), silica gel, cellulose, acrylic acid grafted polypropylene, and the like. Additionally, the solid support contains a reactive moiety suitable for attaching the linking group component. Suitably reactive moieties include, for example, a carboxylic acid, alcohol, amine, halomethyl and the like which is used to covalently attach the linking group component during construction of the present support-bound activators. Many of these supports are available as functional polymers having reactive groups. Examples of such supports, include, by way of example, Acryloyl Wang resin, REM resin, Vinyl polystyrene, Vinylsulfonylmethyl polystyrene, (3-Formylindolyl)acetamidomethyl polystyrene, 2-(3,5-Dimethoxy-4-formylphenoxy)ethoxymethyl polystyrene, 2-(4-Formyl-3-methoxyphenoxy)ethyl polystyrene, 4-(4-Formyl-3-methoxyphenoxy)butyryl AM resin, 4-Benzyloxy-benzaldehyde polystyrene, Aldehyde Wang resin, Formylpolystyrene, 1% DVB, NovaSyn® TG acetal resin, Polystyrene-CHO, Carboxypolystyrene, NovaSyn® TG car- Strongly Acidic Support In another aspect, the present invention provides a strongly acidic support comprising a solid or semi-solid support; and at least one support-bound strongly acid group having the formula:

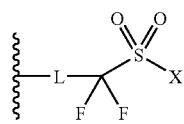

wherein L is a linking group component; and X is OH; and wherein the support-bound strongly acid group is covalently attached to the solid or semi-solid support.

Turning first to the solid or semi-solid support, the present invention is useful in a variety of solid-phase synthesis applications and, accordingly, a variety of supports find utility in boxy resin, Polystyrene-COOH, 4-(2',4'-Dimethoxyphenyl-Fmoc-aminomethyl)phenoxy resin, 4-Methylbenzhydrylamine resin HCl, 4-Methylbenzhydrylamine resin HCl, 9-Fmoc-amino-xanthen-3-yloxy, 9-Fmoc-amino-xanthen-3-yloxy, Amino-(4-methoxyphenyl)methyl polystyrene, Ethylamino-xanthen-3-yloxy-Merrifield resin, NovaSyn® TG Sieber resin, NovaSyn® TGR resin, Rink Amide AM resin, Rink Amide MBHA resin, Rink amide NovaGel™, Rink amide PEGA resin, Rink Amide resin, Sieber Amide resin, Sieber Ethylamide resin, Amino methyl resin, Amino PEGA resin, Aminomethyl NovaGel™, Aminomethylated polystyrene, N-Methylaminomethyl polystyrene, 4-Fmoc-hydrazinobenzoyl AM resin, 1H-Benzotriazole polystyrene, Benzotriazole-5-carbamidomethyl polystyrene, N-Fmoc-N-methoxy-β-alanine AM resin, Weinreb AM resin, 4-Sulfamylbenzoyl AM resin, (±)-1-(2,3-Isopropylidene) glycerol polystyrene, (±)-2,2-Dimethyldioxolan-4-methoxymethyl polystyrene, (±)-1-Glycerol polystyrene, 4-(2',4'-Dimethoxyphenyl-hydroxymethyl)-phenoxy resin, 4-(2',4'-Dimethoxyphenyl-hydroxymethyl)-phenoxy resin, 4-(2',4'-Dimethoxyphenyl-hydroxymethyl)-phenoxy resin, 4-Hydroxymethyl-3-methoxyphenoxybutyric acid AM resin, 4-Hydroxymethyl-3-methoxyphenoxybutyric acid BHA resin, 4-Hydroxymethyl-3-methoxyphenoxybutyric acid MBHA resin, 4-Hydroxymethylphenoxyacetyl NovaGel™, 4-Hydroxymethylphenoxyacetyl PEGA resin, HMP resin, HMPA-NovaGel™, HMPB-AM resin, HMPB-BHA resin, HMPB-MBHA resin, Hydroxy-(2-chlorophenyl)methyl polystyrene, Hydroxymethylpolystyrene, NovaSyn™ TG HMP resin, p-Benzyloxybenzyl Alcohol resin, Polystyrene-CH$_2$OH, Rink Acid resin, Trichloroacetimidate Wang resin, Wang resin, 4-Hydroxymethylbenzoic acid AM resin, 4-Hydroxymethylbenzoic acid NovaGel™, 4-Hydroxymethylbenzoic acid PEGA resin, 4-Hydroxyphenylsulfanylmethyl polystyrene, 9-(Hydroxymethyl)fluorene-4-carboxamidomethyl polystyrene, HESM polystyrene, HMBA-AM resin, HMBA-NovaGel™, HBA-PEGA resin, Hydroxyethylsulfanylmethyl polystyrene, NovaSyn® TG HMBA resin, NovaSyn® TG hydroxy resin, Oxime resin, Aminoethyl photolinker resin, Hydroxyethyl photolinker resins, Hydroxymethyl photolinker resins, 3-[4-(Tritylmercapto)phenyl]propionyl AM resin, Mercaptomethyl polystyrene, NovaSyn® TG tritylthiol resin, Thiol 2-chlorotrityl resin, Thiol 4-methoxytrityl resin, (4-Bromophenyl)diisopropylsilyloxymethyl polystyrene, (4-Formylphenyl)diisopropylsilyloxymethyl polystyrene, (4-Trityloxyphenyl)diisopropylsilyloxymethyl polystyrene. Solid supports also include TENTAGEL™, HYPOGEL™, JANDAJEL™, AND ARGOGEL™. Other solid supports include PEGylated polystyrene (polystyrene derivatized with polyethylene glycol), Tentagel-NH$_2$ resin, and derivatized Tentagel-NH$_2$ resin (e.g., by treatment with acetyl chloride followed by reduction with LiAlH$_4$ to provide Tentagel-NHEt resin). See also the Novabiochem Catalogue 2000 for additional resins and immobilized functional groups.

Such supports may take any size, shape or form, including particulate and non-particulate forms or shapes, spheres, disks, pellets, sheets, plugs, pins, crowns, lanterns, in beaded and non-beaded forms, resins, gels, microspheres, as well as amorphous forms and shapes. Embodiments of particulate supports, include beads, pellets, disks, amorphous particles, or other conventional forms. The solid or semi-solid supports may be used as single particle, as groups of particles, as free flowing particles, and may be packed into columns, tubes or other flow-through devices. In a one embodiment, the diameter of the particulate support is 20-2000 micron, preferably 75-500 micron, more preferably 100-200 micron. As one skilled in the art will readily recognize, the scope of the present invention is not limited to the size, form, or shape of the solid or semi-solid support.

The liking group component can have a variety of structures. The linking group component is one which provides suitable spacing for the activator portion (—CF$_2$—SO$_2$—OH) to interact freely with molecules or reactive components exposed to the activator portion. The linking group component is preferably 6-50 atoms long, more preferably 8-40 atoms long, even more preferably 8-30 atoms long, and yet more preferably 8-20 atoms long, thus providing sufficient exposure for the attached activator portion. Additionally, the linking group component, prior to attachment to the support, will have a attaching portion and a longer chain portion. The attaching portion is that part of the linking group component which can be directly attached to the solid support. This portion can be attached to the solid support via carbon-carbon bonds using, for example, supports having exposed (poly) trifluorochloroethylene moieties, or preferably, by siloxane bonds (using, for example, glass or silicon oxide as the solid support). Siloxane bonds the support are formed in one embodiment via reactions of attaching portions bearing trichlorosilyl or trialkoxysilyl groups. The attaching groups will also have a site for attachment of the longer chain portion. For example, groups which are suitable for attachment to a longer chain portion would include amines, hydroxyl, thiol, and carboxyl.

One skilled in the art will recognize that many additional methods of attaching linkers to solid or semi-solid supports exist. One method uses an amino resin to which an acid-bearing linker is attached via conventional techniques. Another method is the use of aryl ether linkages by coupling a phenol to a Merrifield (or equivalent) resin.

The longer chain portion of the linking group can be any of a variety of molecules which are inert to the subsequent conditions used in the activator reactions described in further detail below. These longer chain portions can be ethylene glycol oligomers containing 2-14 monomer units, or more preferably 2-10 monomer units, and even more preferably 2-8 monomer units; in addition, the longer chain portions can be diamines, diacids, amino acids, peptides, or combinations thereof. In some embodiments, the longer chain portion also comprises an activator enhancing portion, i.e., a portion that increases the reactivity of the activator relative to an alkylene or ethylene glycol linking group. More particularly, an activator enhancing portion is one that provides additional electron withdrawing character to the activator portion (e.g., the —CF$_2$—SO$_2$—OH portion).

In another group of embodiments, L comprises an activator enhancing portion selected from the group consisting of:

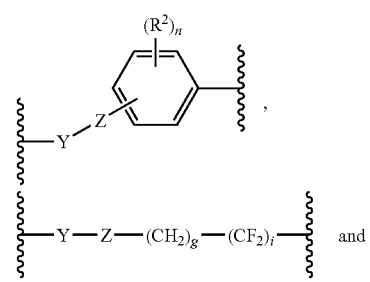

-continued

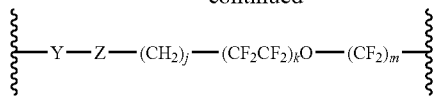

wherein Y is a member selected from the group consisting of a chemical bond, O, CO, S, and NR$^1$; Z is a member selected from the group consisting of a chemical bond or CO; each R$^2$ is independently a member selected from the group-consisting of hydrogen, halogen, (C$_1$-C$_8$)alkyl, (C$_1$-C$_8$)alkoxy, (C$_2$-C$_8$)heteroalkyl, (C$_1$-C$_8$)alkylthio, (C$_1$-C$_8$)alkylamino, di(C$_1$-C$_8$)alkylamino, cyano, nitro and (C$_1$-C$_8$)alkylsulfonyl; the subscript 'g' is an integer selected from the group consisting of 0, 1, 2, 3, 4, 5, 6, 7, 8, 9, and 10; the subscript 'i' is an integer selected from the group consisting of 1, 2, 3, 4, 5, and 6; the subscript 'j' is an integer selected from the group consisting of 0, 1, 2, 3, 4, 5, 6, 7, 8, 9, and 10; the subscript 'k' is an integer selected from the group consisting of 1, 2, 3, and 4; the subscript 'm' is an integer selected from the group consisting of 2 and 3; and the subscript 'n' is an integer selected from the group consisting of 0, 1, 2, 3, and 4. In the groups described herein as dialkylamino, the alkyl groups can be the same or different, or can optionally be combined to form a ring having additional heteroatoms (e.g., pyrrolidino, morpholino, piperazino).

In another group of embodiments, the support-bound activators have a formula selected from:

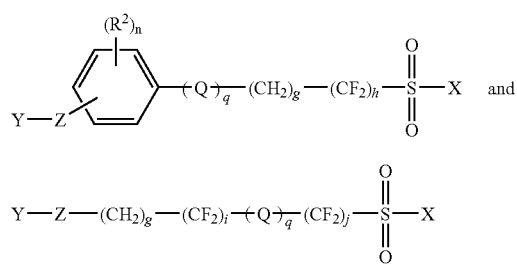

In each of formulae A and B, X is OH; Q is O; Z is a chemical bond or C=O; Y is O-support or NR$_1$-support wherein R$_1$ is H, (C$_1$-C$_8$)alkyl or aryl and the support is a PEG-modified polystyrene or a Merrifield resin; and each le is as defined more generally above. The subscripts in formulae A and B are as follows: 'g' is an integer selected from the group consisting of 0, 1, 2, 3, 4, 5, 6, 7, 8, 9, 10, and 11; 'h' is an integer selected from the group consisting of 1, 2, 3, 4, 5, 6, 7, and 8; 'i' is an integer selected from the group consisting of 0, 1, 2, 3, 4, 5, 6, 7, and 8; 'j' is an integer selected from the group consisting of 1, 2, 3, and 4; 'k' is an integer selected from the group consisting of 1, 2, 3, and 4; 'm' is an integer selected from the group consisting of 2 and 3; 'n' is an integer selected from the group consisting of 0, 1, 2, 3, and 4; and 'q' is an integer selected from the group consisting of 1, and 2.

In one particular embodiment in formulae A and B, X is OH; Q is O; Z is C=O, Y is NH-support wherein the support is a PEG-modified polystyrene; and each R$^2$ is H.

In still other embodiments, each solid or semi-solid support comprises a plurality of support-bound strongly acid groups, with a density of at least 1 μmol support-bound strongly acid groups per gram of solid or semi-solid support, more preferably, at least 1 μmol support-bound strongly acid groups per gram of solid or semi-solid support, and even more preferably, at least 1 mmol support-bound strongly acid groups per gram of solid or semi-solid support.

In another embodiment, the strongly acidic support is available in kit form for use as a reagent or catalyst in solution phase organic chemistry, or as a scavenger resin in solution phase organic chemistry.

Figure 7:
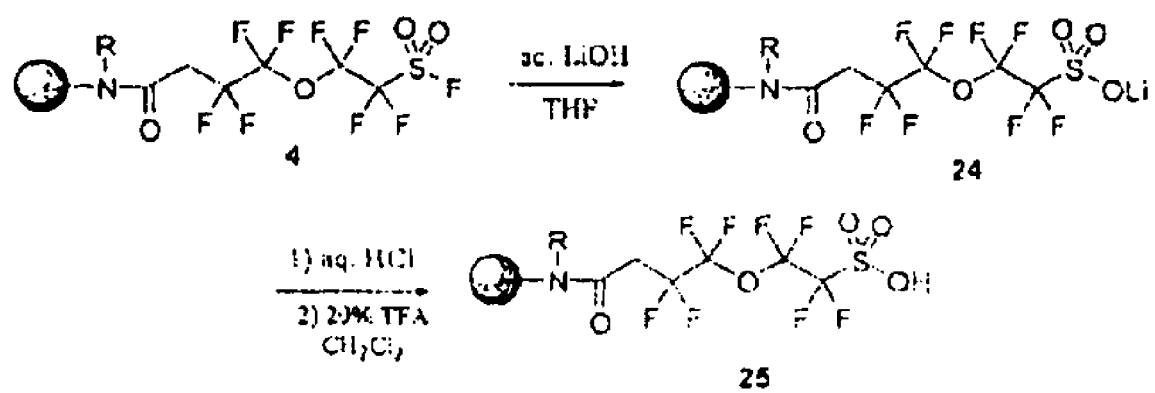
FIG. 7 illustrates the preparation of a perfluorosulfonic acid polymer in accordance with the present invention.

The preparation of the resin-bound perfluorosulfonic acid FIG. 7, Structure 25 is outlined in FIG. 7, and the synthesis of the resin-bound perfluorosulfonic acid FIG. 2, Structure 12 is outlined FIG. 2.

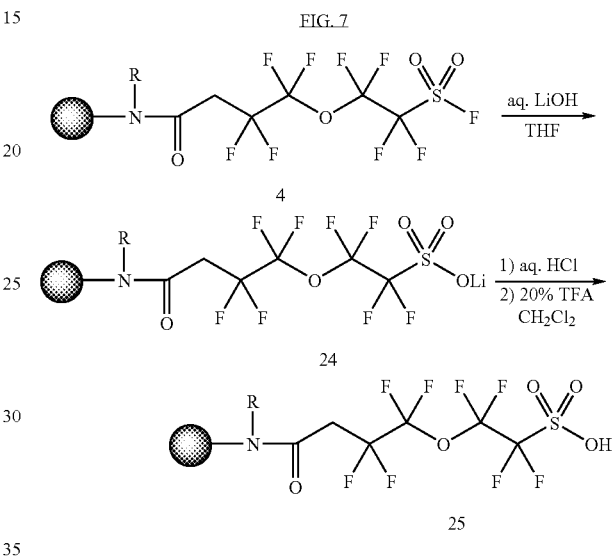

FIG. 7

The highly acidic supports of this invention provide a solid phase reagent that is chemically analogous to perfluorosulfonic acids; furthermore, in one embodiment of the present invention, the vast majority of surface-bound perfluorosulfonic acid sites are readily available for reaction, thus allowing the use of this embodiment both catalytically and stoichiometrically.

In addition to being used as highly acidic solid phase catalysts and reagents, support-bound acidic groups can be used as scavenger resins. Such a use has been described in the generation of diverse collections of compounds. Merely by way of example, "Polymer Supported Reagents Handbook" (NovaBiochem, 2001), is incorporated herein by reference. In general, resins capable of capturing excess reagents, products, or unwanted byproducts from reaction mixtures have found widespread use in organic chemistry laboratories, and in particular, are considered to be highly important in the pharmaceutical arena. These resins can be employed in both covalent and ionic fashions.

For example, an amine can react with an acid chloride to afford an amide as the desired product. The most common method of obtaining the product in a high yield is to use one of the two reaction partners in excess and to then separate the product from excess reagent. When using an excess of the acid chloride, the reaction mixture can be treated with a primary or secondary amine-containing resin after the reaction to covalently capture the excess acid chloride as a polymer bound amide. Simple filtration of the resin from the reaction mixture would afford the desired product amide essentially free of excess acid chloride. Alternatively, when using an excess of the amine component, the reaction mixture can be treated with an acid-containing resin (i.e., a strong cation exchange resin) to ionically capture the excess amine as its ammonium salt form on the resin. Simple filtration of the resin from the reaction mixture would afford the desired amide essentially free of the excess amine.

To date there have been no scavenger resins described containing acidic groups stronger than phenylsulfonic acids (e.g., DOWEX™ (Dow Chemical Company, Midland, Mich.) and related resins). These resins are inherently limited in their ability to capture weakly basic compounds by virtue of their modest acidity. There exists the need to develop resins of much higher acidity (i.e. highly acidic supports) which are swellable in a variety of solvents, capable of achieving high loading (i.e. loading of >0.2 mmol/g, preferably >0.5 mmol/g, more preferably >0.8 mmol/g), and stable to mechanical forces typical during washing steps.

Another application of scavenger supports has been termed "capture and release," a technique in which targets are first captured (i.e., attached to a support) from a chemical reaction solution, then, the unwanted compounds removed by filtration or other similar methods, and finally, the desired compound is released from the support. See Bhat, *J. Comb. Chem.* 2000, 2, 597. This final release step can be performed by a multitude of possible methods depending on the nature of the attachment of the targets to the support. When using resins to "capture" molecules to the support as salts, the displacement step may be conveniently performed by treating the support with a solution containing a volatile amine such as ammonia. Molecules covalently attached to the support can be cleaved under a variety of conditions.

Thus, another embodiment of the polymer-supported compositions described in this is the use of the polymer-supported compositions as either covalent or ionic scavenger resins. An embodiment of this invention is to capture amines, thiols, alcohols, phenols, ketones and other species capable of forming stable triflate products as their respective polymer-supported triflates, and then to filter them away from reaction mixtures. A preferred embodiment of this invention is to expose a reaction mixture containing amine and other basic compounds capable of forming ionic triflate salts with the novel compositions disclosed herein and to then filter away said basic species. See Example 8 below for an illustrative use of the highly acidic supports of the present invention as scavenger resins.

Those skilled in the art will recognize that the polymer-supported perfluorsulfonic acids described herein are dramatically more acidic than the known cation exchange resins, and as such, will be capable of effectively scavenging a broader range of compounds.

Silylating Support

In the field of analytical chemistry, it is common to chemically derivatize molecules to make them more suitable for various chromatographic techniques. The general principles of compound derivatization for chromatography are described in "Handbook of Derivatives for Chromatography: by K. Blau and J. Halket (Wiley, England, 1993), which is incorporated herein by reference. For example, treatment of molecules containing hydroxyl or acid groups with any one of a number of silylating agents renders silyl ethers or esters that are more volatile than the parent compound, and thus more amenable to analysis via gas chromatography. It is also common to derivatize compounds to alter their properties in BPLC applications. One drawback in current methods for compound derivatization is the necessity to separate excess derivatization reagents from the desired, derivatized product. In addition, highly reactive derivatization regents, such as chlorotrimethylsilane and other silylating reagents, have been observed to both deactivate chromatography columns and contaminate flame ionization detectors in gas chromatographs with SiO2 rendering them ineffective. A technique of employing highly reactive, polymer-supported derivatization reagents would be very important and find widespread use through the industry.

One aspect of the present invention provides for a silylating support, and in particular, silylating polymer-supported reagents, that afford the desired derivatized products free of contaminating reagents. Whereas silyltriflates are widely known as extremely reactive silylating reagents in solution, the corresponding polymer-supported silyltriflates have not been widely employed. NAFION™-TMS has been made by Noyori, *Tetrahedron Lett.* 1980, 21, 767 by heating the acid form of the polymer with chlorotrimethylsilane and sulfuric acid. Furthermore, the polymer-supported silyl triflates that have been described in the literature (e.g., Smith, *Tetrahedron Lett.* 1999, 40, 3285 and Porco, *Tetrahedron Lett.* 1999, 40, 3289) are triflating resins and not silylating resins. Thus, there is a need in the art for highly-reactive, silylating resins that are swellable and wettable by organic solvents, and which can thus readily act as stoichiometric silylating reagents. The silylating support of the present invention fulfills this need.

In another aspect, the present invention provides a silylating support comprising a solid or semi-solid support; and at least one support-bound silylating group having the formula:

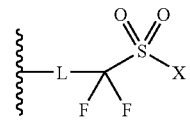

wherein L is a linking group component; X is a trisubstituted silyloxy; wherein the support-bound silylating group is covalently attached to the solid or semi-solid support.

Turning first to the solid or semi-solid support, the present invention is useful in a variety of solid-phase synthesis applications and, accordingly, a variety of supports find utility in this aspect of the invention. Typical solid supports include, but are not limited to, cross-linked divinylbenzene-styrene (polystyrene), controlled pore glass (CPG), polyacrylamides, poly(ethyleneglycol)monomethyl ether and poly(ethylene glycol) (PEG), silica gel, cellulose, acrylic acid grafted polypropylene, and the like. Additionally, the solid support contains a reactive moiety suitable for attaching the linking group component. Suitably reactive moieties include, for example, a carboxylic acid, alcohol, amine, halomethyl and the like which is used to covalently attach the linking group component during construction of the present support-bound activators. Many of these supports are available as functional polymers having reactive groups. Examples of such supports, include, by way of example, Acryloyl Wang resin, REM resin, Vinyl polystyrene, Vinylsulfonylmethyl polystyrene, (3-Formylindolyl)acetamidomethyl polystyrene, 2-(3,5-Dimethoxy-4-formylphenoxy)ethoxymethyl polystyrene, 2-(4-Formyl-3-methoxyphenoxy)ethyl polystyrene, 4-(4-Formyl-3-methoxyphenoxy)butyryl AM resin, 4-Benzyloxy-benzaldehyde polystyrene, Aldehyde Wang resin, Formylpolystyrene, 1% DVB, NovaSyn® TG acetal resin, Polystyrene-CHO, Carboxypolystyrene, NovaSyn® TG carboxy resin, Polystyrene-COOH, 4-(2',4'-Dimethoxyphenyl-Fmoc-aminomethyl)phenoxy resin, 4-Methylbenzhydry-lamine resin HCl, 4-Methylbenzhydrylamine resin HCl, 9-Fmoc-amino-xanthen-3-yloxy, 9-Fmoc-amino-xanthen-3-yloxy, Amino-(4-methoxyphenyl)methyl polystyrene, Ethylamino-xanthen-3-yloxy-Merrifield resin, NovaSyn® TG Sieber resin, NovaSyn® TGR resin, Rink Amide AM resin, Rink Amide MBHA resin, Rink amide NovaGel™, Rink amide PEGA resin, Rink Amide resin, Sieber Amide resin, Sieber Ethylamide resin, Amino methyl resin, Amino PEGA resin, Aminomethyl NovaGel™, Aminomethylated polystyrene, N-Methylaminomethyl polystyrene, 4-Fmoc-hydrazinobenzoyl AM resin, 1H-Benzotriazole polystyrene, Benzotriazole-5-carbamidomethyl polystyrene, N-Fmoc-N-methoxy-β-alanine AM resin, Weinreb AM resin, 4-Sulfamylbenzoyl AM resin, (±)-1-(2,3-Isopropylidene) glycerol polystyrene, (±)-2,2-Dimethyldioxolan-4-methoxymethyl polystyrene, (±)-1-Glycerol polystyrene, 4-(2',4'-Dimethoxyphenyl-hydroxymethyl)-phenoxy resin, 4-(2',4'-Dimethoxyphenyl-hydroxymethyl)-phenoxy resin, 4-(2',4'-Dimethoxyphenyl-hydroxymethyl)-phenoxy resin, 4-Hydroxymethyl-3-methoxyphenoxybutyric acid AM resin, 4-Hydroxymethyl-3-methoxyphenoxybutyric acid BHA resin, 4-Hydroxymethyl-3-methoxyphenoxybutyric acid MBHA resin, 4-Hydroxymethylphenoxyacetyl NovaGel™, 4-Hydroxymethylphenoxyacetyl PEGA resin, HMP resin, HMPA-NovaGel™, HWPBAM resin, HMPB-BHA resin, HMPB-MBHA resin, Hydroxy-(2-chlorophenyl)methyl polystyrene, Hydroxymethylpolystyrene, NovaSyn® TG HMP resin, p-Benzyloxybenzyl Alcohol resin, Polystyrene-CH$_2$OH. Rink Acid resin, Trichloroacetimidate Wang resin, Wang resin, 4-Hydroxymethylbenzoic acid AM resin, 4-Hydroxymethylbenzoic acid NovaGel™, 4-Hydroxymethylbenzoic acid PEGA resin, 4-Hydroxyphenylsulfanylmethyl polystyrene, 9-(Hydroxymethyl)fluorene-4-carboxamidomethyl polystyrene, HESM polystyrene, HMBA-AM resin, HMBA-NovaGel™, HMBA-PEGA resin, Hydroxyethylsulfanylmethyl polystyrene, NovaSyn® TG HMBA resin, NovaSyn® TG hydroxy resin, Oxime resin, Aminoethyl photolinker resin, Hydroxyethyl photolinker resins, Hydroxymethyl photolinker resins, 3-[4-(Tritylmercapto)phenyl]propionyl AM resin, Mercaptomethyl polystyrene, NovaSyn® TG tritylthiol resin, Thiol 2-chlorotrityl resin, Thiol 4-methoxytrityl resin, (4-Bromophenyl)diisopropylsilyloxymethyl polystyrene, (4-Formylphenyl)diisopropylsilyloxymethyl polystyrene, (4-Trityloxyphenyl)diisopropylsilyloxymethyl polystyrene. Solid supports also include TENTAGEL™, HYPOGEL™, JANDAJEL™, AND ARGOGEL™. Other solid supports include PEGylated polystyrene (polystyrene derivatized with polyethylene glycol), Tentagel-NH$_2$ resin, and derivatized Tentagel-NH$_2$ resin (e.g., by treatment with acetyl chloride followed by reduction with LiAlH$_4$ to provide Tentagel-NHEt resin). See also the Novabiochem Catalogue 2000 for additional resins and immobilized functional groups.

Such supports may take any size, shape or form, including particulate and non-particulate forms or shapes, spheres, disks, pellets, sheets, plugs, pins, crowns, lanterns, in beaded and non-beaded forms, resins, gels, microspheres, as well as amorphous forms and shapes. Embodiments of particulate supports, include beads, pellets, disks, amorphous particles, or other conventional forms. The solid or semi-solid supports may be used as single particle, as groups of particles, as free flowing particles, and may be packed into columns, tubes or other flow-through devices. In a one embodiment, the diameter of the particulate support is 20-2000 micron, preferably 75-500 micron, more preferably 100-200 micron. As one skilled in the art will readily recognize, the scope of the present invention is not limited to the size, form, or shape of the solid or semi-solid support.

The linking group component can have a variety of structures. The linking group component is one which provides suitable spacing for the activator portion (—CF$_2$—SO$_2$—OX; wherein X is a trisubstituted silyloxy) to interact freely with molecules or reactive components exposed to the activator portion. The linking group component is preferably 6-50 atoms long, more preferably 8-40 atoms-long, even more preferably 8-30 atoms long, and yet more preferably 8-20 atoms long, thus providing sufficient exposure for the attached activator portion. Additionally, the linking group component, prior to attachment to the support, will have a attaching portion and a longer chain portion. The attaching portion is that part of the linking group component which can be directly attached to the solid support. This portion can be attached to the solid support via carbon-carbon bonds using, for example, supports having exposed (poly)trifluorochloroethylene moieties, or preferably, by siloxane bonds (using, for example, glass or silicon oxide as the solid support). Siloxane bonds the support are formed in one embodiment via reactions of attaching portions bearing trichlorosilyl or trialkoxysilyl groups. The attaching groups will also have a site for attachment of the longer chain portion. For example, groups which are suitable for attachment to a longer chain portion would include amines, hydroxyl, thiol, and carboxyl.

One skilled in the art will recognize that many additional methods of attaching linkers to solid or semi-solid supports exist. One method uses an amino resin to which an acid-bearing linker is attached via conventional techniques. Another method is the use of aryl ether linkages by coupling a phenol to a Merrifield (or equivalent) resin.

The longer chain portion can be any of a variety of molecules which are inert to the subsequent conditions used in the activator reactions described in further detail below. These longer chain portions can be ethylene glycol oligomers containing 2-14 monomer units, or more preferably 2-10 monomer units, and even more preferably 2-8 monomer units; in addition, the longer chain portions can be diamines, diacids, amino acids, peptides, or combinations thereof. In some embodiments, the longer chain portion also comprises an activator enhancing portion, i.e., a portion that increases the reactivity of the activator relative to an alkylene or ethylene glycol linking group. More particularly, an activator enhancing portion is one that provides additional electron withdrawing character to the activator portion (e.g., the —CF$_2$—SO$_2$—OX portion; wherein X is a trisubstituted silyloxy).

In another group of embodiments, L comprises an activator enhancing portion selected from the group consisting of:

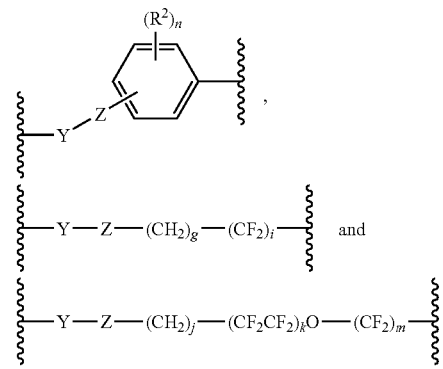

wherein Y is a member selected from the group consisting of a chemical bond, O, CO, S, and NR$^1$; Z is a member selected from the group consisting of a chemical bond or CO; each $R^2$ is independently a member selected from the group consisting of hydrogen, halogen, $(C_1-C_8)$alkyl, $(C_1-C_8)$alkoxy, $(C_2-C_8)$heteroalkyl, $(C_1-C_8)$alkylthio, $(C_1-C_8)$alkylamino, di$(C_1-C_8)$alkylamino, cyano, nitro and $(C_1-C_8)$alkylsulfonyl; the subscript 'g' is an integer selected from the group consisting of 0, 1, 2, 3, 4, 5, 6, 7, 8, 9, and 10; the subscript 'i' is an integer selected from the group consisting of 1, 2, 3, 4, 5, and 6; the subscript 'j' is an integer selected from the group consisting of 0, 1, 2, 3, 4, 5, 6, 7, 8, 9, and 10; the subscript 'k' is an integer selected from the group consisting of 1, 2, 3, and 4; the subscript 'm' is an integer selected from the group consisting of 2 and 3; and the subscript 'n' is an integer selected from the group consisting of 0, 1, 2, 3, and 4. In the groups described herein as dialkylamino, the alkyl groups can be the same or different, or can optionally be combined to form a ring having additional heteroatoms (e.g., pyrrolidino, morpholino, piperazino).

In another group of embodiments, the support-bound activators have a formula selected from:

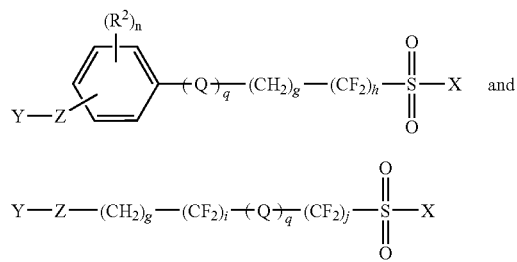

In each of formulae A and B, X is trisubstituted silyloxy; Q is O; Z is a chemical bond or C=O; Y is O-support or $NR_1$-support wherein $R_1$ is H, $(C_1-C_8)$alkyl or aryl and the support is a PEG-modified polystyrene or a Merrifield resin; and each $R^2$ is as defined more generally above. The subscripts in formulae A and B are as follows: 'g' is an integer selected from the group consisting of 0, 1, 2, 3, 4, 5, 6, 7, 8, 9, 10, and 11; 'h' is an integer selected from the group consisting of 1, 2, 3, 4, 5, 6, 7, and 8; 'i' is an integer selected from the group consisting of 0, 1, 2, 3, 4, 5, 6, 7, and 8; 'j' is an integer selected from the group consisting of 1, 2, 3, and 4; 'k' is an integer selected from the group consisting of 1, 2, 3, and 4; 'm' is an integer selected from the group consisting of 2 and 3; 'n' is an integer selected from the group consisting of 0, 1, 2, 3, and 4; and 'q' is an integer selected from the group consisting of 1, and 2.

In one particular embodiment in formulae A and B, X is trisubstituted silyloxy; Q is O; Z is C=O, Y is NH-support wherein the support is a PEG-modified polystyrene; and each $R^2$ is H.

In one embodiment, the trisubstituted silyloxy has the formula $OSiR^3R^4R^5$, wherein, each of $R^3$, $R^4$, and $R^5$ is independently a member selected from the group consisting of substituted $(C_1-C_8)$alkyl, unsubstituted $(C_1-C_8)$alkyl, substituted $(C_1-C_8)$alkenyl, unsubstituted $(C_1-C_8)$alkenyl, substituted aryl, and unsubstituted aryl.

In another embodiment, each of $R^3$, $R^4$, $R^5$ is a methyl group; in another embodiment, each of $R^3$, $R^4$ is a methyl group and $R^5$ is a t-butyl group.

In still other embodiments, each solid or semi-solid support comprises a plurality of support-bound silylating groups, with a concentration of at least 1 mmol support-bound silylating groups per gram of solid or semi-solid support, more preferably, at least 1 μmol support-bound silylating groups per gram of solid or semi-solid support, and even more preferably, at least 1 mmol support-bound silylating groups per gram of solid or semi-solid support.

In another embodiment, the silylating support of the present invention can be provided in kit form for pre-treatment of test compounds prior to analysis by a wide range of analytical chemistry techniques, including gas chromatography and high-performance liquid chromatography. Such a kit could provide the silylating support in the form of a resin or particles packed into a column. The compound to be silylated could then be passed over or through the silylating support prior to analysis by chromatography.

See Example 9 below for one illustrative use of the silylating supports of the present invention.

The following examples provide more detailed descriptions of synthetic methods used to prepare traceless linkers and activators of the present invention. One of skill in the art will appreciate that many of the methods provided below can be applied to the preparation of other linkers and activators. Accordingly, the examples are offered by way of illustration and not by way of limitation.

EXAMPLES

Example 1

This example illustrates the preparation of a polymer-supported perfluorosulfonyl fluoride linker (FIG. 1).

At 0° C., to a stirring solution containing ethyl vinyl ether (600 mg, 8.3 mmol), NaHCO₃ (680 mg, 8.0 mmol), and commercial tetrafluoro-2-(tetrafluoro-2-iodoethoxy)ethanesulfonyl fluoride FIG. 1, Structure 1 (3.5 g, 8.0 mmol) in $CH_3CN$ (8 mL) and $H_2O$ (7 mL) was slowly added $Na_2S_2O_4$ (1.4 g, 8.0 mmol). The reaction mixture was stirred at 5° C. for 50 min. The pH of the reaction mixture was adjusted to 6.2~7.0 by adding 3.0 N aqueous HCl and the mixture was stirred at 25° C. for another 20 min. The reaction mixture was extracted with $CH_2Cl_2$, washed with water and concentrated under reduced pressure. The oily residue was dissolved in acetone (38 mL) and the solution was added to a stirring mixture of 2-methyl-butene-2 (36 mL), $NaH_2PO_4$ (4.0 g, mmol), $NaClO_2$ (5.0 g, mmol) and water (40 mL) at 0-5° C. The reaction mixture was stirred at 5-15° C. for 2 h. The reaction mixture was concentrated under reduced pressure, extracted with ether, washed with brine, dried ($MgSO_4$) and concentrated. The oily crude product was purified on a $SiO_2$ column (MeOH/CHCl₃, 2:98) to give 1.8 g (62%) of the linker FIG. 1, Structure 3 as thick oil. ¹HNMR (CDCl₃, δ): 3.17 (t, J=16.8 Hz, $CF_2CH_2CO_2H$); ¹³C NMR (CDCl₃, δ): 169.54, 36.69, 36.39, 36.09; ¹⁹F NMR (CDCl₃, δ): 121.61 ($SO_2F$), 6.08, 11.51, −36.14, −39.76; MS (ESI) calcd for $C_6H_3F_9O_5S$ 357.96. found: 357.0 (M-H)⁻.

To a stirring solution of the above acid linker FIG. 1, Structure 3 (800 mg, 2.24 mmol) and oxalyl chloride (430 μL, 4.8 mmol) in $CH_2Cl_2$ (1.6 mL) was slowly added DMP (18 μL). After the evolution of gas bubbles, the reaction mixture was stirred for another 1 h and then concentrated under reduced pressure. The oily product was dissolved in $CH_2Cl_2$ (5 mL), the solution was added to a commercial TENTAGEL™ $NH_2$ resin (1.08 g, 0.46 mmol) and the resin was cooled in a dry-ice container for 10 min. To the resin was slowly added diisopropylethylamine (1.2 mL, 7.0 mmol), and the resin was shaken at room temperature overnight. The beads were washed with $CH_2Cl_2$ and dried under vacuum overnight to give resin-bound linker FIG. 1, Structure 4a.

Example 2

This example illustrates the preparation of difluorosulfonic acid linker and the resin-bound difluorosulfonic acid (FIG. 2).

A solution of chloride FIG. 2, Structure 5 (3.8 g, 16.8 mmol) and thiourea (1.3 g, 17 mmol) in EtOH (10 mL) was stirred at 70° C. for 4 h and then cooled to room temperature. A solution of NaOH (1.2 g, 30 mmol) in water (10 mL) was added, and the reaction mixture was stirred at room temperature overnight, concentrated under reduced pressure, acidified to pH 6, extracted with $CH_2Cl_2$, washed with water. The crude thiol FIG. 2, Structure 6 was dissolved in $CH_2Cl_2$ (30 mL), water (30 mL) and acetic acid (2 mL). The solution was cooled to 0-5° C. and $Cl_2$ gas was bubbled onto the solution for 1 h. The reaction mixture was concentrated, extracted with $CH_2Cl_2$, washed with cold water, dried ($MgSO_4$) and concentrated to give sulfonyl chloride FIG. 2, 7 (4.8 g, 97%/o). $^1$H NMR ($CDCl_3$, $\delta$): 1.60 (s, 9H), 4.92 (s, 2H), 7.68 (d, 2H), 8.38 (d, 2H); $^{13}$C NMR ($CDCl_3$, $\delta$): 28.34, 70.52, 81.92, 130.37, 131.44, 134.02, 164.98.

$Et_3N$ (2.0 g, 19.5 mmol) was added to a solution of FIG. 2, 7 (4.2 g, 14 mmol), neopentyl alcohol (2.6 g, 30 mmol) in $CH_2Cl_2$ (20 mL) at −78° C. The reaction mixture was stirred at room temperature overnight, diluted with cold water, extracted with $CH_2Cl_2$, washed with water, dried ($MgSO_4$) and concentrated under reduced pressure to give crude product FIG. 2, 8 as light yellow solid. The crude product was washed with a mixture of hexane and ether (4:1) to yield pure FIG. 2, 8 as off-white powder (4.3 g, 90%/O). $^1$H NMR ($CDCl_3$, $\delta$): 0.96 (s, 9H), 1.60 (s, 9H), 3.78 (s, 2H), 4.40 (s, 2H), 7.44 (d, 2H), 8.02 (d, 2H); $^{13}$C NMR ($CDCl_3$, $\delta$): 26.18, 28.36, 32.03, 56.50, 79.83, 81.64, 130.07, 130.74, 132.48, 132.87, 165.29.

To a solution of the benzylic sulfonate ester FIG. 2, 8 (342 mg, 1.0 mmol) in anhydrous THF at −78° C. was added t-BuLi (620 μL, 1.05 mmol) over a period of 2 min, and the mixture was stirred for 30 min at −78° C. A solution of NFSi (341 mg, 1.05 mmol) in THF (0.5 mL) was added dropwise at −78° C. The mixture was stirred at −78° C. for 1 h. The procedure was repeated with t-BuLi (650 μL, 1.10 mmol) and NFSi (357 mg, 1.10 mmol). The reaction was quenched with water, extracted with $CHCl_3$, washed with water, dried ($MgSO_4$) and concentrated. The crude product was purified on a $SiO_2$ column (MeOH/$CHCl_3$, 2:98) to give pure FIG. 2, 9. A solution of trifluoroacetic acid (1.8 mL) in $CH_2Cl_2$ (4 mL) was added to FIG. 2, 9 and the mixture was stirred for 40 min, concentrated to give FIG. 2, 10 as a white powder (252 mg, 78% from 9). $^1$H NMR ($CD_3COCD_3$, $\delta$): 1.02 (s, 9H), 4.22 (s, 2H), 7.91 (d, 2H), 8.26 (d, 2H).

$Et_3N$ (30 mg, 0.30 mmol) was added to a solution of FIG. 2, 10 (45 mg, 0.14 mmol) and O-(7-azabenzotriazol-1-yl)-N,N,N',N' tetramethyluronium hexafluorophosphate (HATU) (60 mg, 0.16 mmol) in DMF (1.5 mL), and the mixture was added to a TentaGel-$NH_2$ resin (100 mg, 0.043 mmol). The resin was shaken at room temperature overnight, washed with DMF, MeOH and $CH_2Cl_2$, and dried under vacuum to give resin FIG. 2, 11. A solution of LiBr (24 mg, 0.28 mmol) in butane-2-one (1.5 mL) was added to the above resin FIG. 2, 11, and the resin was shaken at 70° C. for 72 h. The beads were washed with butane-2-one, DMF and $CH_2Cl_2$, and dried to give the resin-bound perfluorosulfonic acid FIG. 2, 12.

Example 3

This example illustrates the use of perfluorosulfonyl fluoride linker in deoxygenation of various phenols (FIG. 3).

A mixture of phenol (0.68 mmol), $K_2CO_3$ (100 mg, 0.72 mmol), resin-bound linker FIG. 3, Structure 4 (80 mg, 0.034 mmol) and DMF (1.0 mL) was shaken at room temperature overnight. The resin was washed with water, DMF and $CH_2Cl_2$, and was dried under vacuum overnight to give resin-bound phenol FIG. 3, Structure 13. To the dry resin FIG. 3, Structure 13 were added Pd(OAc)$_2$ (6.0 mg, mmol), 1,3-bis(diphenylphosphino)propane (dppp, 16.0 mg, mmol), DMF (1.2-1.4 mL) and a mixture of $HCO_2H$ (180 μL) and $Et_3N$ (460 μL). The mixture was shaken at 85° C. for 120 min. The polymer beads were filtered and washed with $Et_2O$. The combined organic phase was washed with aqueous $Na_2CO_3$ and water, and evaporated to dryness. The residue was dissolved in $Et_2O$ and eluted through a short column of $SiO_2$ to remove inorganic residues. The crude products were purified by preparative TLC to give the desired products FIG. 3, Structure 14a-1 in >98% purity.

Example 4

This example illustrates the use of the perfluorosulfonyl halide linkers of the invention for the cleavage/cross coupling of polymer-bound phenols using Suzuki coupling reactions (FIG. 4).

The resin-bound phenols FIG. 4, Structure 15 were prepared as described in Example 1. A mixture of the dry resin FIG. 4, Structure 15 (200 mg, 0.07 mmol), Pd(dppf)$Cl_2$ (7.2 mg), boronic acid (0.26 mmol) and $Et_3N$ (88 μL, 0.62 mmol) in DMF (1.5-2.0 mL) was placed in a vial and degassed by blowing $N_2$ with stirring. The vial was sealed and magnetically stirred at 90° C. for 8 h. The polymer beads were filtered and washed with $Et_2O$. The combined organic phase was washed with aqueous $Na_2CO_3$ solution and water, and evaporated under reduced pressure to dryness. The residue was dissolved in $Et_2O$ and eluted through a short bed of $SiO_2$ to remove inorganic residues. The crude products were purified by preparative TLC to give the desired products FIG. 4, Structure 16a-h in >98% purity.

Example 5

This example illustrates the application of the traceless linker technology to the preparation of a library of 10 biaryl compounds, which further illustrate the scope and generality of the linkers (FIG. 5).

The resin-bound aldehyde FIG. 5, Structure 17 was prepared as described in Example 1. To the dry resin FIG. 5, Structure 17 (100 mg, 0.043 mmol) were added amine (0.40 mmol), THF (800 μL), Na(CN)$BH_3$ (1.0 mL) and acetic acid (23 μL). The mixture was shaken at room temperature overnight. The beads were washed with water, DMF, $CH_2Cl_2$ and anhydrous THF, and dried under vacuum overnight to give amine resin FIG. 5, Structure 18. To the dry amine resin FIG. 5, Structure 18 (100 mg, 0.043 mmol) were added $CH_2Cl_2$ (1.2-1.6 mL), acid chloride (0.42 mmol), and the resin was cooled in a dry-ice container for 10 min. To the resin was slowly added diisopropylethylamine (88 μL, 0.5 mmol), and the resin was shaken at room temperature overnight. The beads were washed with water, DMF, $CH_2Cl_2$, and dried under vacuum overnight to give amide resin FIG. 5, Structure 19.

A mixture of the dry resin FIG. 5, Structure 19 (200 mg, 0.07 mmol), Pd(dppf)$Cl_2$ (7.2 mg), boronic acids (0.26 mmol) and $Et_3N$ (88 μL) in DMF (1.0~1.1 mL) was placed in a vial and degassed by blowing $N_2$ with stirring. The vial was sealed and magnetically stirred at 90° C. for 8 h. The polymer beads were filtered and washed with $Et_2O$. The combined organic phase was washed with aqueous Na$_2$CO$_3$ solution and water, and evaporated to dryness. The residue was dissolved in Et$_2$O and eluted through a short bed of SiO$_2$ to remove inorganic residues. The crude products were purified by preparative TLC to give the desired products FIG. 5, Structure 20a-i in >98% purity.

Example 6

This example illustrates the application of perfluorosulfonyl fluoride linker to a multi-step synthesis of the therapeutic agent, meclizine (FIG. 6).

A mixture of 3-methyl-4-hydroxybenzaldehyde (100 mg, 0.72 mmol), K$_2$CO$_3$ (100 mg, 0.72 mmol), resin-bound linker FIG. 6, Structure 4 (100 mg, 0.043 mmol) and DMF (1.1 mL) was shaken at room temperature overnight. The beads were washed with water, DMF and CH$_2$Cl$_2$, and dried under vacuum overnight to give resin FIG. 6, Structure 21. To the dry resin FIG. 6, Structure 21 were added 1-(4-chlorobenzhydryl)piperazine (128 mg, 0.40 mmol), THF (800 µL), Na(CN)BH$_3$ (1.0 mL) and acetic acid (23 µL). The mixture was shaken at room temperature overnight. The beads were washed with water, DME and CH$_2$Cl$_2$, and dried under vacuum overnight to give resin FIG. 6, Structure 22.

To the dry resin FIG. 6, Structure 22 was added Pd(OAc)$_2$ (8.0 mg, mmol), 1,3-bis(diphenyl-phosphino)propane (dppp, 17.0 mg, mmol), DMF (1.4 mL) and a mixture of HCO$_2$H (200 µL) and Et$_3$N (800 µL). The mixture was shaken at 85° C. for 120 min. The polymer beads were filtered and washed with Et$_2$O. The combined organic phase was washed with aqueous Na$_2$CO$_3$ solution and water, and evaporated to dryness. The residue was dissolved in Et$_2$O and eluted through a short column of Al$_2$O$_3$ to remove inorganic residues. The crude products were purified by preparative TLC to give the desired products FIG. 6, Structure 23 in >98% purity. Analytical data of FIG. 6, Structure 23 is identical to that of authentic sample.

Example 7

This example illustrates the preparation of the resin-bound perfluorosulfonic acid (FIG. 7).

A mixture of resin-bound linker FIG. 7, Structure 4 (500 mg, 0.15 mmol), THF (1.0 mL) and 0.6 M LiOH in water (1.2 mL) was shaken at room temperature for 2 h. The beads were washed with water and CH$_2$Cl$_2$, and dried under vacuum overnight to give resin FIG. 7, Structure 24. $^{19}$F NMR (CDCl$_3$, δ): −8.00, −43.44.

To the resin FIG. 6, Structure 24 was added 6 M HCl in water (2.0 mL). The mixture was shaken at room temperature for 6 h. The beads were filtered and washed with CH$_2$Cl$_2$, 20% TFA in CH$_2$Cl$_2$ and CH$_2$Cl$_2$, and dried under vacuum overnight to give resin FIG. 7, Structure 25. $^{19}$F NMR (CDCl$_3$, δ): −8.00, −43.44, −6.84, −7.41, −12.55, −42.36, −42.88.

Example 8

This example illustrates the use of the resin bound perfluorosulfonic acid as a scavenger.

To a solution of benzylamine (0.125 mmol) in 5 mL of THF is added diisopropylethyl amine (0.15 mmol) and benzoylchloride (0.10 mmol). The reaction mixture is stirred at room temperature for 1 hour or until TLC analysis shows consumption of the benzoyl chloride. To this mixture is added perflurosulfonic acid resin prepared in example 8 (3 g, 0.3 mmol/g loading) and the slurry is gently agitated for 1 hour. The slurry is filtered and the resin washed with dichloromethane. The combined filtrates are combined and the solvent removed under reduced pressure to afford N-benzylbenzamide as a solid.

Example 9

This example illustrates the use of the perfluorosulfonyl siloxy resin as a silylating resin.

The free acid resin from example 8 (1 g) is washed with dichloromethane. The resin is treated with a solution of TMS-Cl (10 mmol) in 5 mL of dichloromethane and one drop of concentrated sulfuric acid is added. After being gently agitated for 14 h, the resin is washed with dichloromethane and dried under vacuum.

To a solution of phenol (0.1 mmol) in dichloromethane is added the TMS-resin from above and the resultant slurry is gently agitated for 1 h. The resin is filtered away and the filtrate is either directly submitted for gas chromatographic analysis or the solvent is removed under reduced pressure to yield phenoxytrimethylsilane.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A support-bound activator selected from:

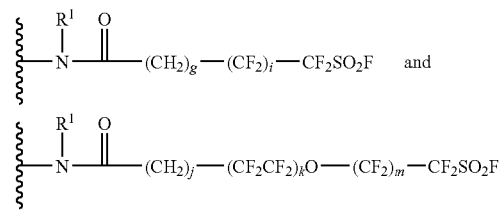

wherein:
R$^1$ is a member selected from the group consisting of H and (C$_1$-C$_8$)alkyl;
the subscript g is an integer selected from the group consisting of 0, 1, 2, 3, 4, 5, 6, 7, 8, 9, and 10;
the subscript i is an integer selected from the group consisting of 1, 2, 3, 4, 5, and 6;
the subscript j is an integer selected from the group consisting of 0, 1, 2, 3, 4, 5, 6, 7, 8, 9, and 10;
the subscript k is an integer selected from the group consisting of 1, 2, 3, and 4; and
the subscript m is an integer selected from the group consisting of 2 and 3; and
wherein the support-bound activator is covalently attached to a solid or semi-solid support, wherein said solid or semi-solid support comprises a material selected from the group consisting of polystyrene, controlled pore glass, polyacrylamide, poly(ethyleneglycol)monomethyl ether, polyethylene glycol, silica gel, cellulose, acrylic acid grafted polypropylene, polystyrene modified by polyethylene glycol, and combinations thereof.

2. A support-bound activator selected from:

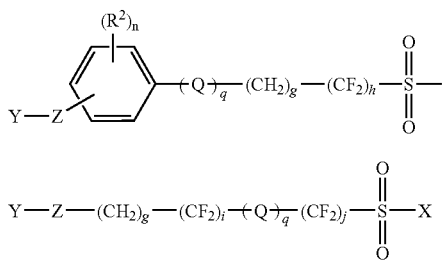

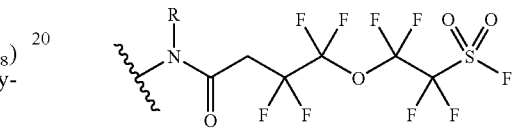

wherein in each of formulae A and B,
X can be F, Cl, trisubstituted silyloxy, or OH;
Q is O;
Z is a chemical bond or C=O;
Y is O-support or $NR_1$-support wherein $R_1$ is H, ($C_1$-$C_8$) alkyl or aryl and the support is a PEG-modified polystyrene or a Merrifield resin; and
each $R^2$ is independently a member selected from the group consisting of hydrogen, halogen, ($C_1$-$C_8$)alkyl, ($C_1$-$C_8$) alkoxy, ($C_2$-$C_8$)heteroalkyl, ($C_1$-$C_8$)alkylthio, ($C_1$-$C_8$) alkylamino, di($C_1$-$C_8$)alkylamino, cyano, nitro and ($C_1$-$C_8$)alkylsulfonyl;

'g' is an integer selected from the group consisting of 0, 1, 2, 3, 4, 5, 6, 7, 8, 9, 10, and 11;
'h' is an integer selected from the group consisting of 1, 2, 3, 4, 5, 6, 7, and 8;
'i' is an integer selected from the group consisting of 0, 1, 2, 3, 4, 5, 6, 7, and 8;
'j' is an integer selected from the group consisting of 1, 2, 3, and 4;
'n' is an integer selected from the group consisting of 0, 1, 2, 3, and 4; and
'q' is an integer selected from the group consisting of 1 and 2.

3. The support-bound activator according to claim 2 wherein X is F; Q is O; Z is C=O, Y is NH-support wherein the support is a PEG-modified polystyrene; and each $R^2$ is H.

4. A support-bound activator having the following formula:

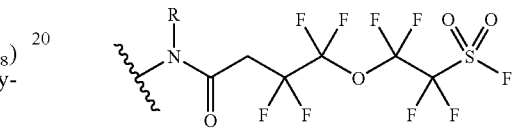

wherein R is hydrogen or ethyl.

* * * * *